United States Patent [19]

Lunkenheimer et al.

[11] Patent Number: 5,585,395
[45] Date of Patent: Dec. 17, 1996

[54] SUBSTITUTED BENZIMIDAZOLES USEFUL AS PEST CONTROL AGENTS

[75] Inventors: Winfried Lunkenheimer, Wuppertal; Bernd Baasner, Bergisch Gladbach; Folker Lieb, Leverkusen; Christoph Erdelen, Leichlingen; Ulrike Wachendorff-Neumann, Bonn; Wilhelm Stendel, Wuppertal; Ulrich Görgens, Ratingen, all of Germany

[73] Assignee: Bayer Aktiengesellschaft, Leverkusen, Germany

[21] Appl. No.: 424,256

[22] PCT Filed: Oct. 25, 1993

[86] PCT No.: PCT/EP93/02947

§ 371 Date: Apr. 24, 1995

§ 102(e) Date: Apr. 24, 1995

[87] PCT Pub. No.: WO94/11350

PCT Pub. Date: May 26, 1994

[30] Foreign Application Priority Data

Nov. 6, 1992 [DE] Germany .................. 42 37 597.5

[51] Int. Cl.[6] .................. A61K 31/415; A01N 43/52; C07D 235/10
[52] U.S. Cl. .................. 514/395; 548/302.1; 548/309.7; 504/276
[58] Field of Search .................. 548/309.7, 302.1; 514/395; 504/276

[56] References Cited

U.S. PATENT DOCUMENTS 3,823,154 7/1974 Corbett et al. .................. 260/309.2
3,980,784 9/1976 Peterson .................. 424/273
4,622,323 11/1986 Giraudon et al. .................. 514/228

FOREIGN PATENT DOCUMENTS 6501323 8/1966 Netherlands.

OTHER PUBLICATIONS

CA 66:28771p (8)1967.

*Primary Examiner*—Jacqueline Haley
*Assistant Examiner*—Laura L. Stockton
*Attorney, Agent, or Firm*—Sprung Horn Kramer & Woods

[57] ABSTRACT

The invention relates to new substituted benzimidazoles of the general formula (I)

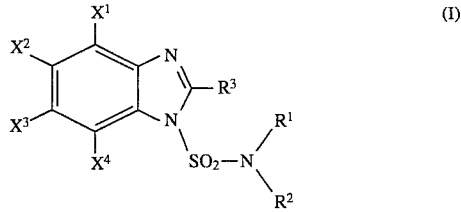

wherein $R^1$, $R^2$, $R^3$, $X^1$, $X^2$, $X^3$ and $X^4$ have the meanings given in the disclosure, which are useful as pest control agents, and to a process for their preparation.

3 Claims, No Drawings

SUBSTITUTED BENZIMIDAZOLES USEFUL AS PEST CONTROL AGENTS

This application is a 371 of PCT/EP 93/02947 filed Oct. 25, 1993.

The invention relates to new substituted benzimidazoles, to a number of processes for their preparation and to their use as pest control agents.

It is known that certain phosphoric acid esters or carbamates, such as, for example, the compound O,S-dimethyl-thiolo-phosphoramide or the compound N-methyl-O-(2-isopropoxyphenyl)carbamate have insecticidal properties (cf. e.g. DE 12 10 835 and DE 11 08 202, respectively).

The level and/or duration of action of these previously known compounds, however, in particular in the case of certain insects or at low application concentrations, is not completely satisfactory in all areas of application.

New substituted benzimidazoles have been found of the general formula (I)

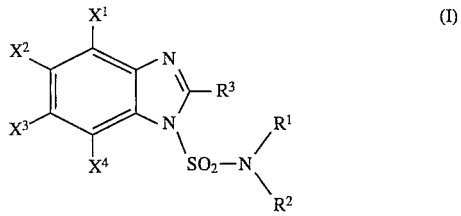

in which

R$^1$ represents hydrogen, alkyl, halogenoalkyl, cycloalkyl or optionally substituted aryl, R$^2$ represents hydrogen, alkyl, halogenoalkyl, cycloalkyl or optionally substituted aryl, R$^3$ represents fluoroalkyl and X$^1$, X$^2$, X$^3$ and X$^4$ independently of one another in each case represent hydrogen, halogen, cyano, nitro, in each case optionally substituted alkyl, alkoxy, alkylthio, alkylsulphinyl, alkylsulphonyl or cycloalkyl, dioxyalkylene which is optionally substituted and may be fused on, hydroxycarbonyl, alkylcarbonyl, alkoxycarbonyl, cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but with at least one of the substituents X$^1$, X$^2$, X$^3$ and X$^4$ being different from hydrogen, with the exception of the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethylbenzimidazole.

Depending on the nature and number of the substituents, the compounds of the formula (I) may optionally be present as geometrical and/or optical isomers or regioisomers, or mixtures of these isomers in varying composition. Both the pure isomers and the isomer mixtures are claimed according to the invention.

It has also been found that the new substituted benzimidazoles of the general formula (I)

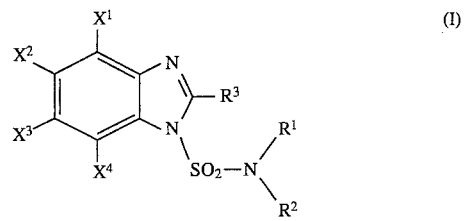

in which

R$^1$ represents hydrogen, alkyl, halogenoalkyl, cycloalkyl or optionally substituted aryl, R$^2$ represents hydrogen, alkyl, halogenoalkyl, cycloalkyl or optionally substituted aryl, R$^3$ represents fluoroalkyl and X$^1$, X$^2$, X$^3$ and X$^4$ independently of one another each case represent hydrogen, halogen, cyano, nitro, in each case optionally substituted alkyl, alkoxy, alkylthio, alkylsulphinyl, alkylsulphonyl or cycloalkyl, dioxyalkylene which is optionally substituted and may be fused on, hydroxycarbonyl, alkylcarbonyl, alkoxycarbonyl, cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but with at least one of the substituents X$^1$, X$^2$, X$^3$ and X$^4$ being different from hydrogen, with the exception of the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethylbenzimidazole, are obtained if 1H-benzimidazoles of the formula (II)

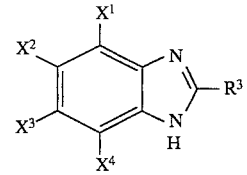

in which

R$^3$, X$^1$, X$^2$, X$^3$ and X$^4$ have the meaning given above are reacted with halogenosulphonamides of the formula (III)

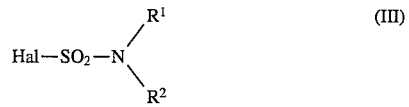

in which

Hal represents halogen and

R$^1$ has the meaning given above and

R$^2$ has the meaning given above, optionally in the presence of a diluent and optionally in the presence of a reaction auxiliary.

Finally it has been found that the new substituted benzimidazoles of the general formula (I) have a good activity against pests.

Surprisingly, the substituted benzimidazoles of the general formula (I) according to the invention display a considerably improved insecticidal activity, in comparison to the phosphoric acid esters or carbamates known from the prior art, such as, for example, the compound O,S-dimethyl-thiolo-phosphoramide or the compound N-methyl-O-(2-isopropoxyphenyl)carbamate, which in terms of their action are closely related compounds, A general definition of the substituted benzimidazoles according to the invention is given by the formula (I). Preferred compounds of the formula (I) are those in which $R^1$ represents hydrogen, straight-chain or branched alkyl having 1 to 8 carbon atoms, straight-chain or branched halogenoalkyl having 1 to 8 carbon atoms and 1 to 17 identical or different halogen atoms, cycloalkyl having 3 to 8 carbon atoms, or aryl having 6 to 10 carbon atoms which is optionally substituted once or more than once by identical or different substituents, possible substituents of aryl being:

halogen, cyano, nitro, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl having in each case 1 to 6 carbon atoms in the individual alkyl moities, divalent dioxyalkylene having 1 to 5 carbon atoms which is optionally substituted once or more than once by identical or different substituents comprising halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally substituted once or more than once by identical or different substituents comprising halogen and/or straight-chain or branched alkyl having 1 to 6 carbon atoms and/or straight-chain or branched halogenoalkyl having 1 to 6 carbon atoms and 1 to 13 identical or different halogen atoms, $R^2$ represents hydrogen, straight-chain or branched alkyl having 1 to 8 carbon atoms, straight-chain or branched halogenoalkyl having 1 to 8 carbon atoms and 1 to 17 identical or different halogen atoms, cycloalkyl having 3 to 8 carbon atoms or aryl having 6 to 10 carbon atoms which is optionally substituted once or more than once by identical or different substituents, possible aryl substituents being those mentioned for $R^1$, $R^3$ represents straight-chain or branched fluoroalkyl having 1 to 8 carbon atoms and 1 to 17 fluorine atoms, and $X^1$, $X^2$, $X^3$ and $X^4$ independently of one another in each case represent hydrogen, fluorine, chlorine, bromine, iodine, cyano, nitro, in each case straight-chain or branched alkyl, alkoxy, alkylthio, alkylsulphinyl or alkylsulphonyl having in each case 1 to 8 carbon atoms, cycloalkyl having 3 to 8 carbon atoms, in each case straight-chain or branched halogenoalkyl, halogenoalkoxy, halogenoalkylthio, halogenoalkylsulphinyl, halogenoalkylsulphonyl having in each case 1 to 6 carbon atoms and 1 to 13 identical or different halogen atoms, or divalent dioxyalkylene having 1 to 5 carbon atoms which is optionally substituted once or more than once by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, or else represents hydroxycarbonyl, in each case straight-chain or branched alkylcarbonyl or alkoxycarbonyl having in each case 1 to 6 carbon atoms in the alkyl moiety, cycloalkyloxycarbonyl having 3 to 8 carbon atoms in the cycloalkyl moiety, amino or aminocarbonyl which are each optionally substituted once or more than once by identical or different substituents, possible substituents of amino in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl moieties, or arylcarbonyl, arylsulphonyl, arylaminocarbonyl or arylmethylsulphonyl having in each case 6 to 10 carbon atoms in the aryl moiety and each of which is optionally substituted in the aryl moiety once or more than once by identical or different substituents, possible substituents of aryl being in each case those mentioned for $R^1$;

or else represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 to 10 carbon atoms in the aryl moiety and in each case optionally substituted in the aryl moiety once or more than once by identical or different substituents, possible substituents for aryl being being in each case those mentioned for $R^1$, but with at least one of the substituents $X^1$, $X^2$, $X^3$ and $X^4$ being different from hydrogen, and with the exception of the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethyl-benzimidazole.

Particularly preferred compounds of the formula (I) are those in which $R^1$ represents hydrogen, straight-chain or branched alkyl having 1 to 6 carbon atoms, straight-chain or branched halogenoalkyl having 1 to 6 carbon atoms and 1 to 13 identical or different halogen atoms, cycloalkyl having 3 to 7 carbon atoms, or aryl having 6 or 10 carbon atoms which is optionally substituted once to five times by identical or different substituents, possible substituents of aryl being:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl moities, divalent di-oxyalkylene having 1 to 4 carbon atoms which is optionally substituted once to six times by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally substituted once to five times by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydrogen, straight-chain or branched alkyl having 1 to 6 carbon atoms, straight-chain or branched halogenoalkyl having 1 to 6 carbon atoms and 1 to 13 identical or different halogen atoms, cycloalkyl having 3 to 7 carbon atoms or aryl having 6 or 10 carbon atoms which is optionally substituted once to five times by identical or different substituents, possible substituents of aryl being those mentioned for $R^1$, $R^3$ represents straight-chain or branched fluoroalkyl having 1 to 6 carbon atoms and 1 to 13 fluorine atoms, and $X^1$, $X^2$, $X^3$ and $X^4$ independently of one another in each case represent hydrogen, fluorine, chlorine, bromine, cyano, nitro, in each case straight-chain or branched alkyl, alkoxy, alkylthio, alkylsulphinyl or alkylsulphonyl having in each case 1 to 6 carbon atoms, cycloalkyl having 3 to 7 carbon atoms, in each case straight-chain or branched halogenoalkyl, halogenoalkoxy, halogenoalkylthio, halogenoalkylsulphinyl, halogenoalkylsulphonyl having in each case 1 to 4 carbon atoms and 1 to 9 identical or different halogen atoms, or divalent dioxyalkylene having 1 to 4 carbon atoms which is optionally substituted once to six times by identical or different substituents comprising halogen and/or straight-chain or branched alkyl having 1 to 4 carbon atoms and/or straight-chain or branched halogenoalkyl having 1 to 4 carbon atoms and 1 to 9 identical or different halogen atoms, or else represents hydroxycarbonyl, in each case straight-chain or branched alkylcarbonyl or alkoxycarbonyl having in each case 1 to 4 carbon atoms in the alkyl moiety, cycloalkyloxycarbonyl having 3 to 7 carbon atoms in the cycloalkyl moiety, or amino or aminocarbonyl which are in each case optionally substituted once or twice by identical or different substituents, possible substituents of amino in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl having in each case 1 to 4 carbon atoms in the individual alkyl moieties, or arylcarbonyl, arylsulphonyl, arylaminocarbonyl or arylmethylsulphonyl having in each case 6 or 10 carbon atoms in the aryl moiety in each case optionally substituted in the aryl moiety once to five times by identical or different substituents, possible substituents of aryl being in each case those mentioned for $R^1$;

or else represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 or 10 carbon atoms in the aryl moiety and in each case optionally substituted in the aryl moiety once to five times by identical or different substituents, possible substituents of aryl being in each case those mentioned for $R^1$, but with at least one of the substituents $X^1$, $X^2$, $X^3$ and $X^4$ being different from hydrogen, and with the exception of the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethylbenzimidazole.

Aryl radicals which can be mentioned are phenyl or naphthyl.

Particularly preferred compounds of the formula (I) are those in which $R^1$ represents hydrogen, straight-chain or branched alkyl having 1 to 4 carbon atoms, straight-chain or branched halogenoalkyl having 1 to 4 carbon atoms and 1 to 9 identical or different halogen atoms, cycloalkyl having 3 to 6 carbon atoms, or phenyl which is optionally substituted once to three times by identical or different substituents, possible substituents of phenyl being:
halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl having in each case 1 to 3 carbon atoms in the individual alkyl moieties, divalent dioxyalkylene having 1 to 3 carbon atoms which is optionally substituted once to four times by identical or different substituents comprising halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally substituted once to three times by identical or different substituents comprising halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydrogen, straight-chain or branched alkyl having 1 to 4 carbon atoms, straight-chain or branched halogenoalkyl having 1 to 4 carbon atoms and 1 to 9 identical or different halogen atoms, cycloalkyl having 3 to 6 carbon atoms or phenyl which is optionally substituted once to three times by identical or different substituents, possible substituents of phenyl being those mentioned for $R^1$, $R^3$ represents straight-chain or branched fluoroalkyl having 1 to 4 carbon atoms and 1 to 9 fluorine atoms, and $X^1$, $X^2$, $X^3$ and $X^4$ independently of one another in each case represent hydrogen, chlorine, bromine, cyano, nitro, in each case straight-chain or branched alkyl, alkoxy, alkylthio, alkylsulphinyl or alkylsulphonyl having in each case 1 to 4 carbon atoms, cycloalkyl having 3, 5 or 6 carbon atoms, in each case straight-chain or branched halogenoalkyl, halogenoalkoxy, halogenoalkylthio, halogenoalkylsulphinyl, halogenoalkylsulphonyl having in each case 1 to 3 carbon atoms and 1 to 7 identical or different halogen atoms, or divalent dioxyalkylene having 1 to 3 carbon atoms which is optionally substituted once to four times by identical or different substituents comprising halogen and/or straight-chain or branched alkyl having 1 to 3 carbon atoms and/or straight-chain or branched halogenoalkyl having 1 to 3 carbon atoms and 1 to 7 identical or different halogen atoms, or else represents hydroxycarbonyl, in each case straight-chain or branched alkylcarbonyl or alkoxycarbonyl having in each case 1 to 3 carbon atoms in the alkyl moiety, cycloalkyloxycarbonyl having 3, 5 or 6 carbon atoms in the cycloalkyl moiety, or amino or aminocarbonyl each of which is optionally substituted once or twice by identical or different substituents, possible substituents of amino in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl having in each case 1 to 3 carbon atoms in the individual alkyl moieties, or phenylcarbonyl, phenylsulphonyl, phenylaminocarbonyl or phenylmethylsulphonyl which are in each case optionally substituted once to three times by identical or different substituents, possible substituents of phenyl in each case being those mentioned for $R^1$;

or else represent phenyl, phenyloxy, phenylthio, phenylsulphinyl, phenylsulphonyl, phenylsulphonyloxy, phenylcarbonyl, phenyloxycarbonyl, phenylthiomethylsulphonyl or phenylazo which are in each case optionally substituted in the phenyl moiety once to three times by identical or different substituents, possible substituents of phenyl being being in each case those mentioned for $R^1$, but with at least one of the substituents $X^1$, $X^2$, $X^3$ and $X^4$ being different from hydrogen, and with the exception of the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethyl-benzimidazole.

In addition to the compounds mentioned in the Preparation Examples, detailed mention may be made of the following substituted benzimidazoles of the general formula (I):

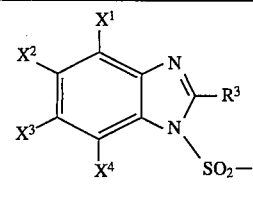

(I)

| $X^1$ | $X^2$ | $X^3$ | $X^4$ | $R^1$ | $R^2$ | $R^3$ |
|---|---|---|---|---|---|---|
| Br | H | $CF_3$ | H | $CH_3$ | $CH_3$ | $C_2F_5$ |
| Br | H | $CF_3$ | H | $CH_3$ | $CH_3$ | $C_3F_7$ |
| Br | H | $CF_3$ | H | $CH_3$ | $CH_3$ | $C_7F_{15}$ |
| $CF_3$ | H | $CF_3$ | H | $CH_3$ | $CH_3$ | $CF_3$ |
| $CF_3$ | H | $CF_3$ | H | $CH_3$ | $CH_3$ | $C_2F_5$ |
| $CF_3$ | H | $CF_3$ | H | $CH_3$ | $CH_3$ | $C_3F_7$ |
| $CF_3$ | H | $CF_3$ | H | $CH_3$ | $CH_3$ | $C_7F_{15}$ |
| Cl | H | $SCF_3$ | H | $CH_3$ | $CH_3$ | $CF_3$ |
| Cl | H | $SCF_3$ | H | $CH_3$ | $CH_3$ | $C_2F_5$ |
| Cl | H | $SCF_3$ | H | $CH_3$ | $CH_3$ | $C_3F_7$ |
| Cl | H | $SCF_3$ | H | $CH_3$ | $CH_3$ | $C_7F_{15}$ |
| Br | H | $SCF_3$ | H | $CH_3$ | $CH_3$ | $CF_3$ |
| Br | H | $SCF_3$ | H | $CH_3$ | $CH_3$ | $C_2F_5$ |
| Br | H | $SCF_3$ | H | $CH_3$ | $CH_3$ | $C_3F_7$ |
| Br | H | $SCF_3$ | H | $CH_3$ | $CH_3$ | $C_7F_{15}$ |
| COO-n-$C_4H_9$ | H | $CF_3$ | H | $CH_3$ | $CH_3$ | $CF_3$ |
| COO-n-$C_4H_9$ | H | $CF_3$ | H | $CH_3$ | $CH_3$ | $C_2F_5$ |
| COO-n-$C_4H_9$ | H | $CF_3$ | H | $CH_3$ | $CH_3$ | $C_3F_7$ |
| COO-n-$C_4H_9$ | H | $CF_3$ | H | $CH_3$ | $CH_3$ | $C_7F_{15}$ |
| H | $CF_3$ | $CF_3$ | H | $CH_3$ | $CH_3$ | $CF_3$ |
| H | $CF_3$ | $CF_3$ | H | $CH_3$ | $CH_3$ | $C_2F_5$ |
| H | $CF_3$ | $CF_3$ | H | $CH_3$ | $CH_3$ | $C_3F_7$ |
| H | $CF_3$ | $CF_3$ | H | $CH_3$ | $CH_3$ | $C_7F_{15}$ |
| H | $OCF_3$ | $OCF_3$ | H | $CH_3$ | $CH_3$ | $C_2F_5$ |
| H | $OCF_3$ | $OCF_3$ | H | $CH_3$ | $CH_3$ | $C_3F_7$ |
| H | $OCF_3$ | $OCF_3$ | H | $CH_3$ | $CH_3$ | $C_7F_{15}$ |
| H | $-O-CF_2-CF_2-O-$ | | H | $CH_3$ | $CH_3$ | $C_2F_5$ |
| H | $-O-CF_2-CF_2-O-$ | | H | $CH_3$ | $CH_3$ | $C_3F_7$ |
| H | $-O-CF_2-CF_2-O-$ | | H | $CH_3$ | $CH_3$ | $C_7F_{15}$ |
| H | Cl | $SCF_3$ | H | $CH_3$ | $CH_3$ | $CF_3$ |
| H | Cl | $SCF_3$ | H | $CH_3$ | $CH_3$ | $C_2F_5$ |
| H | Cl | $SCF_3$ | H | $CH_3$ | $CH_3$ | $C_3F_7$ |
| H | Cl | $SCF_3$ | H | $CH_3$ | $CH_3$ | $C_7F_{15}$ |
| H | $SCF_3$ | Cl | H | $CH_3$ | $CH_3$ | $CF_3$ |
| H | $SCF_3$ | Cl | H | $CH_3$ | $CH_3$ | $C_2F_5$ |
| H | $SCF_3$ | Cl | H | $CH_3$ | $CH_3$ | $C_3F_7$ |
| H | $SCF_3$ | Cl | H | $CH_3$ | $CH_3$ | $C_7F_{15}$ |
| H | Br | $SCF_3$ | H | $CH_3$ | $CH_3$ | $CF_3$ |
| H | Br | $SCF_3$ | H | $CH_3$ | $CH_3$ | $C_2F_5$ |
| H | Br | $SCF_3$ | H | $CH_3$ | $CH_3$ | $C_3F_7$ |
| H | Br | $SCF_3$ | H | $CH_3$ | $CH_3$ | $C_7F_{15}$ |
| H | $SCF_3$ | Br | H | $CH_3$ | $CH_3$ | $CF_3$ |
| H | $SCF_3$ | Br | H | $CH_3$ | $CH_3$ | $C_2F_5$ |
| H | $SCF_3$ | Br | H | $CH_3$ | $CH_3$ | $C_3F_7$ |
| H | $SCF_3$ | Br | H | $CH_3$ | $CH_3$ | $C_7F_{15}$ |

The 1H-benzimidazoles of the formula (II) mentioned in the preparation of the substituted benzimidazoles of the formula (I) can also, like the compounds of the formula (I), be employed as agents for combating pests. Preferred in this context are 1H-benzimidazoles of the formula (II) in which the substituents have the preferred and particularly preferred meanings listed for the compounds of the formula (I). The following compounds of the formula (I) are mentioned individually:

| $X^1$ | $X^2$ | $X^3$ | $X^4$ | Z |
|---|---|---|---|---|
| H | $CF_3$ | Br | H | $CF_3$ |
| H | $-O-C(CF_3)(CH_2-CF_3)-O-$ | | H | $CF_3$ |
| H | $-OCF_3$ | Cl | H | $CF_3$ |
| H | $-OCF_3$ | Br | H | $CF_3$ |
| H | $-O-CFCl-CFCl-O-$ | | H | $CF_3$ |
| Br | H | $CF_3$ | H | $C_7F_{15}$-n |

Using for example, 5,6-dichloro-2-trifluoromethyl-benzimidazole and N,N-diethylchlorosulphonamide as starting compounds, the course of reaction of the process according to the invention can be represented by the following formula scheme:

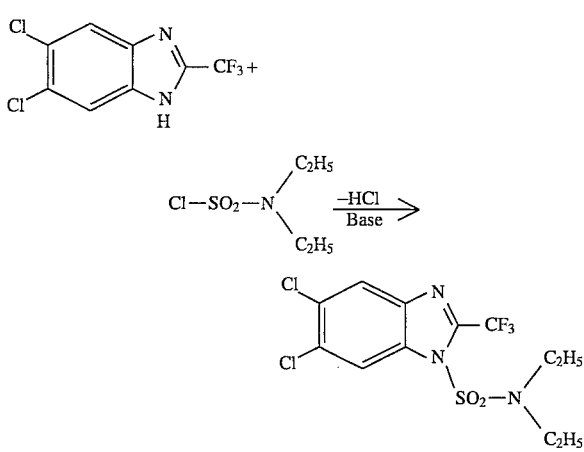

A general definition of the 1H-benzimidazoles required as starting substances for carrying out the process according to the invention is given by the formula (II). In this formula (II), $R^3$, $X^1$, $X^2$, $X^3$ and $X^4$ preferably represent those radicals which have already been mentioned as preferred for these substituents in connection with the description of the compounds of the formula (I) according to the invention.

The 1H-benzimidazoles of the formula (II) are known or can be obtained by analogy with known processes (cf. e.g. J. Amer. Chem. Soc. 75, 1292 [1953]; U.S. Pat. No. 3,576, 818).

A general definition of the halogenosulphonamides also required as starting materials for carrying out the process according to the invention is given by the formula (III). In this formula (III), $R^1$ and $R^2$ preferably represent those radicals which have already been mentioned as preferred for these substituents in connection with the description of the substances of the formula (I) according to the invention.

Hal represents preferably fluorine, chlorine or bromine, in particular chlorine or bromine.

The compounds of the formula (III) are compounds of organic chemistry which are known in general, or are obtainable by analogy with generally known processes.

Suitable diluents for carrying out the process according to the invention are inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, or bases such as pyridine.

The process according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholates, acetates, carbonates or hydrogen carbonates, such as, for example, sodium hydride, sodium amide, lithium diethylamide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, organolithium compounds such as n-butyllithium, and tertiary amines such as trimethylamine, triethylamine, tributylamine, di-isopropylethylamine, tetramethylguanidine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

The process according to the invention can optionally also be carried out in a two-phase system such as, for example, water/toluene or water/dichloromethane, optionally in the presence of a suitable phase-transfer catalyst. Examples of such catalysts which may be mentioned are: tetmbutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyldimethyl-ammonium methyl sulphate, dimethyl-$C_{12}$/$C_{14}$-alkylbenzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out the process according to the invention, the reaction temperatures can be varied over a wide range. It is in general carded out at temperatures of between −70° C. and +200° C., preferably at temperatures of between 0° C. and 130° C.

The process according to the invention is usually carried out under atmospheric pressure. However, it is also possible to work under increased or reduced pressure.

To carry out the process according to the invention requires the use, per mol of 1H-benzimidazole of the formula (II), of in general from 1.0 to 5.0 tool, preferably from 1.0 to 2.5 mol, of halogenosulphonamides of the formula (III) and optionally of from 0.01 to 5.0 mol, preferably from 1.0 to 3.0 mol, of reaction auxiliary.

The implementation of the reaction, work-up and isolation of the reaction products are carried out by known methods (cf. also in this respect the Preparation Examples).

The purification of the end products of the formula (I) is carded out using conventional methods, for example by column chromatography or by recrystallization.

Characterization is made on the basis of the melting point or, in the case of non-crystallizing compounds—especially for regioisomer mixtures—using proton nuclear magnetic resonance spectroscopy ($^1$H-NMR).

The active substances are suitable for combating animal pests, preferably arthropods and nematodes, in particular insects and arachnids, which are encountered in agriculture, in forests, in the protection of stored goods and materials, and in the hygiene sector. They are effective against normally sensitive and resistant species and against all or individual development stages.

The abovementioned pests include:

From the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and Scutigera spec.;

from the order of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example, *Forficula auricularia;* from the order of the Isoptera, for example, Reticulitermes spp.;

from the order of the Anoplura, for example, *Phylloxera vastatrix,* Pemphigus spp., Pediculus humanus corporis, Haematopinus spp. and Linognathus spp.;

from the order of the Mallophaga, for example, Trichodectes spp. and Damalinea spp.; from the order of the Thysanoptera, for example, *Hercinothrips femoralis* and *Thrips tabaci;* from the order of the Heteroptera, for example, Eurigaster spp., *Dysdercus intermedius, Piesma quadrata, Cimex lectularius, Rhodnius prolixus* and Triatoma spp.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomo, Eriosoma lanigerum, Hyalopterus, arundinis, Macrosiphum avenae,* Myzus spp., *Phorodon humuli, Rhopalosiphum padi,* Empoasca spp., *Euscelis bilobatus, Nephotettix cinciceps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example, Diprion spp., Hoplocampa spp., Lasius spp., *Monomorium pharaonis* and Vespa spp.; from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cutereba spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example, *Xenopsylla cheopis* and Ceratophyllus spp.;

from the order of the Arachnida, for example, *Scorpio maurus* and *Latrodectus mactans;* from the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active substances according to the invention are active not only against pests in plants, hygiene and stored goods but also, in the veterinary sector, against animal parasites (ectoparasites and endoparasites) such as ixodic ticks, argasid ticks, scab mites, trombiculid mites, flies (piercing and lapping), parasitizing fly larvae, lice, biting lice, feather lice, fleas and worms which live as endoparasites.

They are active against normally sensitive and resistant species and strains, and against all parasitizing and non-parasitizing development stages of the ecto- and endoparasites.

The active substances according to the invention are distinguished by a high insecticidal activity.

They can be employed with particularly good success for combating phytopathogenic insects, such as, for example, against the caterpillars of the cabbage moth (*Plutella maculipennis*) or against the tobacco budworm (*Heliothis virescens*) and for combating phytopathogenic mites such as, for example, red spider mites (*Tetranychus urticae*).

In addition, the active substances according to the invention can also be employed for controlling pests in hygiene and stored goods, such as, for example, against the house fly (*Musca domestica*) or against species of cockroaches such as, for example, *Periplaneta americana.*

Moreover, the active substances according to the invention can also be employed with particularly good success for combating pests which live as parasites of warm-blooded creatures, such as, for example, against scab mites (*Psoroptes ovis*).

The 1H-benzimidazoles of the formula (II), which are used as precursors, also possess a good insecticidal activity.

In addition, the active substances according to the invention also possess good fungicidal activity and can be employed with particularly good success for controlling cereal diseases, such as, for example, against the causative organism of powdery mildew in cereals (*Erysiphe graminis*) or against the causative organism of net blotch disease in barley (*Pyrenophora teres*) or against the causative organism of glume blotch in wheat (*Septoria nodorum*) or for controlling diseases in rice, such as, for example, against the causative organism of rice blast disease (*Pyricularia oryzae*). In addition, the active substances according to the invention also possess a good in vitro activity.

Moreover, the active substances according to the invention, at appropriate application rates, also possess herbicidal activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the me of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carders there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and tin.

The formulations in general contain between 0.1 and 95 per cent by weight of active compound, preferably between 0.5 and 90%.

The active substances according to the invention can be present in their commercially available formulations and in the use forms prepared from these formulations, as a mixture with other active substances such as insecticides, attractants, sterilizers, acaricides, nematicides, fungicides, growth-regulating substances or herbicides. The insecticides include, for example, phosphates, carbamates, carboxylic acid esters, chlorinated hydrocarbons, phenylureas, substances produced by microorganisms, etc.

The active substances according to the invention can also be present in their commercially available formulations and in the use forms prepared from these formulations, as a mixture with synergists. Synergists are compounds by means of which the action of the active substances is increased without the synergist added necessarily having an active effect itself.

The content of active substance of the use forms prepared from the commercially available formulations may vary within a wide range. The active substance concentration of the use forms may be from 0.0000001 up to 95 per cent by weight of active substance, preferably between 0.0001 and 1 per cent by weight.

Application is carried out in a conventional manner appropriate to the use forms.

When used against pests in hygiene and stored goods the active substances are notable for an outstanding residual action on wood and clay and for a good alkali stability on limed substrates.

The active substances which can be used in accordance with the invention are also suitable for controlling insects, mites, ticks etc. in the sector of animal husbandry and cattle rearing, the combating of the pests enabling better results to be achieved, e.g. higher milk yields, greater weight, more attractive coats, longer lifetime etc.

The application of the active substances which can be used in accordance with the invention is carded out in this sector in a known manner, for example by oral administration in the form of tablets, capsules, drinking formulations or granules, by dermal or external administration in the form, for example, of dipping, spraying, application by pouring (pour-on or spot-on) and powdering, and by parenteral administration in the form, for example, of injection, and furthermore by the feed-through method. In addition to this, application as a shaped article (neckband, ear-tag) is also possible.

The preparation and the use of the active substances according to the invention is evident from the following examples.

PREPARATION EXAMPLES

Example 1

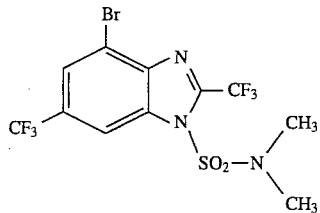

6.6 g (0.045 mol) of dimethylsulphamoyl chloride are added dropwise with stirring at room temperature to a mixture of 10.2 g (0.03 mol) of 2,6-bis-(trifluoromethyl)-4-bromo-1H-benzimidazole, 8.4 g (0.06 mol) of powdered potassium carbonate and 100 ml of acetonitrile and, after addition is complete, the mixture is heated for 6 hours at reflux temperature. For working up, the reaction mixture is cooled and filtered, the filtrate is concentrated in vacuo and the residue is purified by chromatography on silica gel (eluent: dichloromethane).

7.7 g (58% of theory) of 2,6-bis-(trifluoromethyl)-4-bromo-1-dimethylsulphamoylbenzimidazole are obtained with a melting point of 144°–147° C.

In a corresponding manner, and in accordance with the general instructions of preparation, the following substituted benzimidazoles of the general formula (I) are obtained:

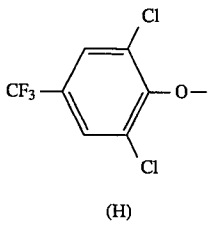

(I)

| Ex. No. | $X^1$ | $X^2$ | $X^3$ | $X^4$ | $R^1$ | $R^2$ | $R^3$ | physical properties |
|---|---|---|---|---|---|---|---|---|
| 2 | H | 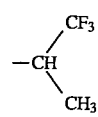 (H) | H 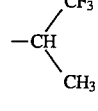 | H | $CH_3$ | $CH_3$ | $CF_3$ | $^1$H-NMR*): 2.91; 6.85–7.88 |
| 3 | H | F (H) | H (F) | H | $CH_3$ | $CH_3$ | $CF_3$ | $^1$H-NMR*): 2.78; 7.32–8.1 |
| 4 | H | F (H) | H (F) | H | H | 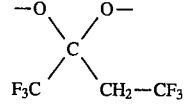 | $CF_3$ | MS: m/e = 379 (M⁺, 100%) |
| 5 | H | $NO_2$ (H) | H ($NO_2$) | H | H | 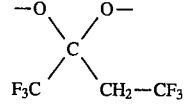 | $CF_3$ | MS: m/e = 310 (M⁺, 100%) |
| 6 | H | $NO_2$ (H) | H ($NO_2$) | H | $CH_3$ | $CH_3$ | $CF_3$ | $^1$H-NMR*): 2.95; 7.81–8.58 |
| 7 | H | Cl (H) | H (Cl) | H | $CH_3$ | $CH_3$ | $CF_3$ | $^1$H-NMR*): 2.89; 7.31–7.91 |
| 8 | H | | $-O-CF_2-O-$ | H | $CH_3$ | $CH_3$ | $CF_3$ | m.p. 179° C. |
| 9 | H | | 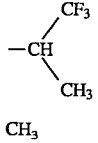 | H | $CH_3$ | $CH_3$ | $CF_3$ | $^1$H-NMR*): 3.04; 7.35; 7.58; 3.055 |
| 10 | H | $CF_3$ (H) | H ($CF_3$) | H | $CH_3$ | $CH_3$ | $CF_3$ | $^1$H-NMR*): 2.91; 7.21–8.01 |
| 11 | H | $CF_3$ (H) | H ($CF_3$) | H | H | 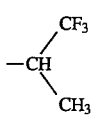 | $CF_3$ | MS: m/e = 249 (M⁺, 100%) |
| 12 | H | $CF_3$ (Br) | Br ($CF_3$) | H | $CH_3$ | $CH_3$ | $CF_3$ | $^1$H-NMR*): A: 2.80; 7.91 8.11 B: 2.81, 7.94; 8.08 |
| 13 | H | $CF_3$ (Cl) | Cl ($CF_3$) | H | H | 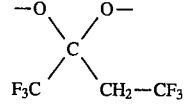 | $CF_3$ | $^1$H-NMR*): A: 7.85; 8.10 B: 7.99; 8.00 |
| 14 | H | $CF_3$ (Cl) | Cl ($CF_3$) | H | $CH_3$ | $CH_3$ | $CF_3$ | $^1$H-NMR*): A: 2.81; 7.82; 8.06 B: 2.83; 7.99; 8.01 |

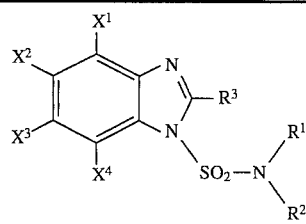

(I)

| Ex. No. | $X^1$ | $X^2$ | $X^3$ | $X^4$ | $R^1$ | $R^2$ | $R^3$ | physical properties |
|---|---|---|---|---|---|---|---|---|
| 15 | H | | $-O-CH_2-CH_2-O-$ | H | $CH_3$ | $CH_3$ | $CF_3$ | m.p. 147° C. |
| 16 | H | | $-O-CF_2-CHF-O-$ <br> $(-O-CHF-CF_2-O-)$ | H | $CH_3$ | $CH_3$ | $CF_3$ | 3.07; 6.05; 7.62; 7.78 |
| 17 | H | | $-O-CF_2-CClF-O-$ <br> $(-O-CClF-CF_2-O-)$ | H | $CH_3$ | $CH_3$ | $CF_3$ | m.p. 105° C. |
| 18 | H | $CF_3O$ (H) | H $(CF_3O)$ | H | $CH_3$ | $CH_3$ | $CF_3$ | $^1$H-NMR*): 2.98; 7.30–7.62 |
| 19 | H | $CF_3O$ | $CF_3O$ | H | $CH_3$ | $CH_3$ | $CF_3$ | $^1$H-NMR*): 2.96; 7.75; 7.93 |
| 20 | H | $CF_3$ $(CH_3O)$ | $CH_3O$ $(CF_3)$ | H | $CH_3$ | $CH_3$ | $CF_3$ | $^1$H-NMR*): 5.49; 5.53; 6.61–8.11 |
| 21 | H | $C_2H_5O-CO-$ (H) | H $(C_2H_5O-CO-)$ | H | $CH_3$ | $CH_3$ | $CF_3$ | |
| 22 | H | $C_6H_5-CO-NH-$ (H) | H $(C_6H_5-CO-NH-)$ | H | $CH_3$ | $CH_3$ | $CF_3$ | $^1$H-NMR*): 22.79; 7.60–8.31; 10.45 |
| 23 | H | $(CH_3)_2N-CO-$ (H) | H $((CH_3)_2N-CO-)$ | H | $CH_3$ | $CH_3$ | $CF_3$ | |
| 24 | H | $F_2CH-CF_2-O-$ (H) | H $(F_2CH-CF_2-O-)$ | H | $CH_3$ | $CH_3$ | $CF_3$ | $^1$H-NMR*): 3.12; 5.96; 7.28–8.03 |
| 25 | H | $C_6H_5-SO_2-NH-$ (H) | H $(C_6H_5-SO_2-NH-)$ | H | $CH_3$ | $CH_3$ | $CF_3$ | |
| 26 | H | $CF_3S$ (H) | H $(CF_3S)$ | H | $CH_3$ | $CH_3$ | $CF_3$ | $^1$H-NMR*): 3.01; 7.58–7.92 |
| 27 | H | COOH (H) | H (COOH) | H | $CH_3$ | $CH_3$ | $CF_3$ | |

*)The $^1$H-NMR spectra were recorded in deuterochloroform (CDCl$_3$) or hexadeuterodimethyl sulphoxide (DMSO-d$_6$) using tetramethylsilane (TMS) as the internal standard. The value given is the chemical shift d in ppm.

In a corresponding manner, the following substituted benzimidazoles of the formula (Ia) are also obtained:

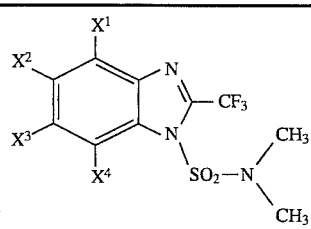

(Ia)

| Ex. No. | $X^1$ | $X^2$ | $X^3$ | $X^4$ | physical properties |
|---|---|---|---|---|---|
| 28 | H | ![CF3-phenyl-SO2-NH-] (H) ( alternative ) | H | H | $^1$H-NMR*): 2.81; 7.01–7.98 |

-continued
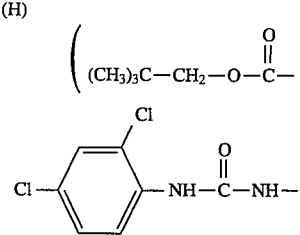
(Ia)
| Ex. No. | X¹ | X² | X³ | X⁴ | physical properties |
|---|---|---|---|---|---|
| 29 | H | (CH₃)₃C—CH₂—O—C(=O)—  (H) ((CH₃)₃C—CH₂—O—C(=O)—) | H | H | $^1$H-NMR*): 3.02; 7.57–8.79 |
| 30 | H | 2,4-Cl₂-C₆H₃-NH-C(=O)-NH—  (H) (2,4-Cl₂-C₆H₃-NH-C(=O)-NH—) | H | H | $^1$H-NMR*): 2.85; 7.18–8.03 |
| 31 | H | (F₃C-CH₂)(F₃C)C(O-)(O-)-C₆H₃-NH-C(=O)-NH—  (H) ((F₃C-CH₂)(F₃C)C(O-)(O-)-C₆H₃-NH-C(=O)-NH—) | H | H | MS: m/e = 642 (M⁺); 200 (100%) |
| 32 | H | 3-Cl-4-(C₂H₅O-(CH₂)₂-O)-C₆H₃-NH-C(=O)-NH—  (H) (3-Cl-4-(C₂H₅O-(CH₂)₂-O)-C₆H₃-NH-C(=O)-NH—) | H | H | $^1$H-NMR*): 2.98; 6.81–8.11 |
| 33 | H | 3-Cl-4-(n-C₃H₇O-(CH₂)₂-O)-C₆H₃-NH-C(=O)-NH—  (H) (3-Cl-4-(n-C₃H₇O-(CH₂)₂-O)-C₆H₃-NH-C(=O)-NH—) | H | H | |

-continued (Ia)

Structure: benzimidazole with X¹, X², X³, X⁴ substituents, CF₃ group, and SO₂-N(CH₃)₂ group.

| Ex. No. | X¹ | X² | X³ | X⁴ | physical properties |
|---------|----|----|----|----|---------------------|
| 34 | H | C₂H₅O—(CH₂)₂—O—C₆H₄—NH—C(O)—NH— (H) (C₂H₅O—(CH₂)₂—O—C₆H₄—NH—C(O)—NH—) | H | H | ¹H-NMR*): 3.08; 6.86–8.18 |
| 35 | H | i-C₃H₇O—(CH₂)₂—O—C₆H₄—NH—C(O)—NH— (H) (i-C₃H₇O—(CH₂)₂—O—C₆H₄—NH—C(O)—NH—) | H | H | |
| 36 | H | 4-Cl-C₆H₄—CH₂—SO₂—N(CH₂—OC₂H₅)— (H) (4-Cl-C₆H₄—CH₂—SO₂—N(CH₂—OC₂H₅)—) | H | H | ¹H-NMR*): 2.88; 7.21–7.78; 9.50 |
| 37 | H | C₆H₅—CH₂—SO₂—NH— (H) (C₆H₅—CH₂—SO₂—NH—) | H | H | ¹H-NMR*): 2.83; 6.39–7.82 |
| 38 | H | 4-O₂N—C₆H₄—C(O)—NH— (H) (4-O₂N—C₆H₄—C(O)—NH—) | H | H | ¹H-NMR*): 2.81; 7.58–8.38 |
| 39 | H | 2-Cl-C₆H₄—C(O)—NH— | H | H | ¹H-NMR*): 2.82; 7.29–8.75 |

(Ia)

| Ex. No. | X¹ | X² | X³ | X⁴ | physical properties |
|---------|----|----|----|----|---------------------|
| (H) | ![2-chlorobenzamido group: C₆H₄(Cl)-C(O)-NH-] | | | | |

*)The ¹H-NMR spectra were recorded in deuterochloroform (CDCl₃) or hexadeuterodimethyl sulphoxide (DMSO-d6) using tetramethylsilane (TMS) as the interanl standard. The value given is the chemical shift d in ppm.

PREPARATION OF THE STARTING COMPOUND

Example II-1

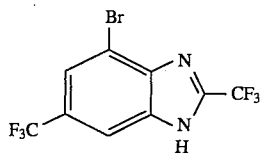

382 g (2.5 mol) of phosphorus oxychloride are added dropwise with stirring at room temperature to a mixture of 290 g (1 mol) of 3-bromo-5-trifluoromethyl-o-phenylenediamine hydrochloride, 150 g (1.42 mol) of trifluoroacetic acid and 1.4 l of 1,2-dimethoxyethane, and the mixture is subsequently stirred for 6 hours at 60° C. and a further 15 hours at room temperature. For working up, the solvent and excess phosphorus oxychloride are distilled off, the residue is stirred into 600 ml of ice-water and extracted three times with 500 ml of ethyl acetate each time: the combined organic phases are dried and concentrated in vacuo and the residue is purified by chromatography on silica gel (eluent: cyclohexane/ethyl acetate 2:1 ).

237 g (72% of theory) of 2,6-bis-(trifluoromethyl)-4-bromo-1H-benzimidazole are obtained with a melting point of 127°–130° C.

In a corresponding manner, the following substituted 1H-benzimidazoles of the general formula (II) are obtained:

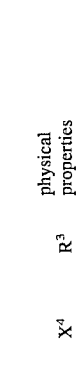

| Ex. No. | X¹ | X² | X³ | X⁴ | R³ | physical properties |
|---|---|---|---|---|---|---|
| II-2 | H | 2,6-dichloro-4-CF₃-phenoxy (H) | H | H | CF₃ | m.p. 227° C. |
| II-3 | H | F | H | H | CF₃ | m.p. 213° C. |
| II-4 | H | (H)/NO₂ | (F) | H | CF₃ | m.p. 151° C. |
| II-5 | H | (H) | H | H | CF₃ | m.p. 193° C. |
| II-6 | Cl | Cl | (NO₂) | H | CF₃ | m.p. 165–170° C. |
| II-7 | (H) | H | H | (Cl) | CF₃ | m.p. 195–199° C. |
| II-8 | Br | (Cl) | (H) | H | CF₃ | m.p. 120–122° C. |
| II-9 | (H) | Cl | Cl | (Br) | CF₃ | m.p. 145–149° C. |
| II-10 | H | H | H | H | CF₃ | m.p. 197–200° C. |
| II-11 | H | (C₆H₅—CO—) | C₆H₅—CO— | H | CF₃ | m.p. >230° C. |
| II-12 | Br | CH₃—CO— | H | H | CF₃ | m.p. 180–187° C. |
| II-13 | (H) | (H) | (CH₃—CO—) | (Br) | CF₃ | m.p. 209° C. |
| II-14 | H | Cl—CH₂—SO₂— | Cl—CH₂—SO₂— | H | CF₃ | m.p. 242° C. |
| II-15 | H | H | Br | H | CF₃ | m.p. 235–237° C. |
| | | (Cl—CH₂—SO₂—) | (H) | | | |
| | | CF₃ | (CF₃) | | | |
| | | (Br) | | | | |

—O—CH₂—CH₂—CH₂—O—

—O—CF₂—O—
—O—CF₂—CF₂—O—

-continued (II)

Structure: benzimidazole with substituents X¹ (4-position), X² (5-position), X³ (6-position), X⁴ (7-position), and R³ at 2-position of the imidazole ring (NH).

| Ex. No. | X¹ | X² | X³ | X⁴ | R³ | physical properties |
|---|---|---|---|---|---|---|
| II-16 | H | —O—CF$_2$—CHF—O— (—O—CHF—CF$_2$—O—) | | H | CF$_3$ | m.p. 217° C. |
| II-17 | H | CF$_3$O | Cl | H | CF$_3$ | m.p. 185° C. |
| II-18 | H | (Cl) | (CF$_3$O) | H | CF$_3$ | m.p. 144° C. |
| II-19 | H | —O—CFCl—CFCl—O— | | H | CF$_3$ | m.p. 209° C. |
| II-20 | H | $\begin{array}{c}\text{O}\\ \diagup\; \diagdown \\ \text{F}_3\text{C}-\text{C}-\text{CH}_2-\text{CF}_3 \\ \diagdown \; \diagup \\ \text{O} \end{array}$ | | H | CF$_3$ | m.p. 168° C. |
| II-21 | H | CF$_3$O | H | H | CF$_3$ | m.p. 158° C. |
| II-22 | (CF$_3$) | (H) | (CF$_3$O) | CF$_3$ (H) | CF$_3$ | m.p. 105° C. |
| II-23 | H | CH$_3$—SO$_2$— (CH$_3$O) | CH$_3$O (CF$_3$) | H | CF$_3$ | m.p. 60° C. |
| II-24 | H | (C$_2$H$_5$)N—CO— (H) | H | H | CF$_3$ | m.p. 125° C. |
| II-25 | H | C$_2$H$_5$O—CO— (H) | ((C$_2$H$_5$)N—CO—) | H | CF$_3$ | m.p. 140° C. |
| II-26 | H | C$_6$H$_5$—CO—NH— (H) | C$_2$H$_5$O—CO— | H | CF$_3$ | m.p. 202° C. |
| II-27 | H | CH$_3$O—CO— (H) | C$_6$H$_5$—CO—NH— | H | CF$_3$ | m.p. 157° C. |
| II-28 | H | (CH$_3$)$_2$N—CO— (H) | CH$_3$O—CO— | H | CF$_3$ | m.p. 226–227° C. |
| II-29 | H | F$_2$CH—CF$_2$—O— (H) | ((CH$_3$)$_2$N—CO—) | H | CF$_3$ | m.p. 181° C. |
| II-30 | H | C$_6$H$_5$—SO$_2$—NH— (H) | F$_2$CH—CF$_2$—O— | H | CF$_3$ | m.p. 99° C. |
| II-31 | H | 2-Cl-C$_6$H$_4$—SO$_2$—NH— | (C$_6$H$_5$—SO$_2$—NH—) H | H | CF$_3$ | m.p. 67° C. |

-continued (II) benzimidazole structure with X¹, X², X³, X⁴ on benzene ring and R³ on 2-position

| Ex. No. | X¹ | X² | X³ | X⁴ | R³ | physical properties |
|---|---|---|---|---|---|---|
| II-32 | H | 2-CF₃-C₆H₄-SO₂-NH- (H) | 2-Cl-C₆H₄-SO₂-NH- (H) | H | CF₃ | m.p. 79° C. |
| II-33 | H | (CH₃)₃C-CH₂-O-C(=O)- (H) | H | H | CF₃ | m.p. 214–215° C. |
| II-34 | H | 2,4-Cl₂-C₆H₃-NH-C(=O)-NH- (H) | 2,4-Cl₂-C₆H₃-NH-C(=O)-NH- | H | CF₃ | m.p. 254–255° C. |

-continued
(II)
| Ex. No. | X¹ | X² | X³ | X⁴ | R³ | physical properties |
|---|---|---|---|---|---|---|
| II-35 | H |  | H | H | CF₃ | m.p. 103° C. |
| II-36 | H |  | H | H | CF₃ | m.p. 186° C. |
| II-37 | H | 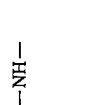 | H | H | CF₃ | m.p. 144° C. |

-continued (II)

Structure: benzimidazole with R³ at 2-position, X¹ at 4, X² at 5, X³ at 6, X⁴ at 7.

| Ex. No. | X¹ | X² | X³ | X⁴ | R³ | physical properties |
|---|---|---|---|---|---|---|
| II-38 | H | C₂H₅O—(CH₂)₂—O—C₆H₄—NH—C(=O)—NH— (H) | H | H | CF₃ | m.p. 207° C. |
| II-39 | H | i-C₃H₇O—(CH₂)₂—O—C₆H₄—NH—C(=O)—NH— (H) | H | H | CF₃ | m.p. 201° C. |
| II-41 | H | (CF₃)₂N— (H) | H ((CF₃)₂N—) | H | CF₃ | |
| II-42 | H | C₆H₅—CH₂—SO₂—NH— (H) | H | H | CF₃ | m.p. 68° C. |
| II-43 | H | CF₃S (H) | H (CF₃S) | H | CF₃ | m.p. 174° C. |
| II-44 | H | FClCH—CF₂—O— (H) | H (FClCH—CF₂—O—) | H | CF₃ | m.p. 157° C. |

-continued
(II)
| Ex. No. | X¹ | X² | X³ | X⁴ | R³ | physical properties |
|---|---|---|---|---|---|---|
| II-45 | H | 2,4-Cl₂-C₆H₃-NH-C(=O)-NH- (H) | H | H | CF₃ | m.p. 176° C. |
| II-46 | H | CH₃-SO₂-NH-C₆H₄-SO₂-NH- (H) | H | H | CF₃ | |
| II-47 | H | C₆H₅-NH-C(=O)-NH- (H) | H | H | CF₃ | m.p. 190° C. |
| II-48 | H | CH₃O-(CH₂)₂-O-C₆H₄-NH-C(=O)-NH- | H | H | CF₃ | m.p. 208° C. |

-continued (II)

| Ex. No. | X¹ | X² | X³ | X⁴ | R³ | physical properties |
|---|---|---|---|---|---|---|
| II-49 | H | (H) | CH₃O—(CH₂)₂—O—⟨C₆H₄⟩—NH—C(=O)—NH— | H | CF₃ | m.p. 162° C. |
| II-50 | H | (CH₃)₃C—O—CO— (H) | H ((CH₃)₃C—O—CO—) | H | CF₃ | m.p. 70° C. |
| II-52 | H | 2-COOCH₃-C₆H₄-SO₂-NH— (H) | (2-COOCH₃-C₆H₄-SO₂-NH—) H | H | CF₃ | m.p. 194° C. |
| II-53 | H | 4-O₂N-C₆H₄-C(=O)-NH— (H) | (4-O₂N-C₆H₄-C(=O)-NH—) H | H | CF₃ | m.p. 220° C. |
| II-53 | H | 2-Cl-C₆H₄-C(=O)-NH— | | | | |

-continued $$\text{(II)}$$

Structure: benzimidazole with X¹, X², X³, X⁴ on benzene ring and R³ at 2-position

| Ex. No. | X¹ | X² | X³ | X⁴ | R³ | physical properties |
|---|---|---|---|---|---|---|
| II-54 | H | CH₃O—CO—N(CH₃)—SO₂—NH— (H) | (H) CH₃O—CO—N(CH₃)—SO₂—NH— [2-Cl-C₆H₄-C(O)-NH-] | H | CF₃ | |
| II-55 | H | COOH (H) | H (COOH) | H | CF₃ | m.p. 250° C. |
| II-56 | H | (CH₃)₃C—NH—CO— (H) | H (((CH₃)₃C—NH—CO—)) | H | CF₃ | m.p. 187° C. |
| II-57 | H | F₃C—C(CH₃)₂—NH—C(O)— (H) | H [F₃C—C(CH₃)₂—NH—C(O)—] | H | CF₃ | m.p. 167° C. |
| II-58 | H | NC—CH₂— (H) | H (NC—CH₂—) | H | CF₃ | |
| II-59 | H | NH₂ (H) | H (NH₂) | H | CF₃ | |
| II-60 | H | HOOC—CH₂— (H) | H (HOOC—CH₂—) | H | CF₃ | |
| II-61 | H | F₃C—SO₂— (H) | H (F₃C—SO₂—) | H | CF₃ | |
| II-62 | H | H₃C—SO₂— (H) | H (H₃C—SO₂—) | H | CF₃ | m.p. 143° C. |
| II-63 | H | H (C₆H₅) | C₆H₅ (H) | H | CF₃ | m.p. 177-182° C. |

-continued (II)

[Structure: benzimidazole with X¹, X², X³, X⁴ substituents on benzene ring and R³ on 2-position]

| Ex. No. | X¹ | X² | X³ | X⁴ | R³ | physical properties |
|---|---|---|---|---|---|---|
| II-64 | H | $C_2H_5O$ (H) | H ($C_2H_5O$) | H | $CF_3$ | m.p. 86–90° C. |
| II-65 | H | $CH_3O$ | $CH_3O$ | H | $CF_3$ | m.p. 184–188° C. |
| II-66 | H | H ($CH_3O$) | $CH_3O$ (H) | H | $CF_3$ | m.p. 144–146° C. |
| II-67 | H | H ($c$-$C_6H_{11}$) | $c$-$C_6H_{11}$ (H) | H | $CF_3$ | m.p. 198–200° C. |
| II-68 | H | H ($t$-$C_4H_9$) | $t$-$C_4H_9$ (H) | H | $CF_3$ | m.p. <50° C. |
| II-69 | $CH_3$ (H) | H | H | H ($CH_3$) | $CF_3$ | m.p. 139–142° C. |
| II-70 | Br (H) | $CH_3O$ | $CH_3O$ | H (Br) | $CF_3$ | m.p. 183–185° C. |
| II-71 | H | $CH_3O$ | $CH_3O$ | Br | $CF_3$ | m.p. 83–87° C. |
| II-72 | H | H ($CH_3$) | $CH_3$ (H) | H | $CF_3$ | m.p. 182° C. |
| II-73 | H | H ($CH_3O$) | $CH_3O$ (H) | H | $CF_3$ | m.p. 160° C. |

*) The ¹H-NMR spectra were recorded in deuterochloroform ($CDCl_3$) or hexadeutero-dimethyl sulphoxide (DMSO-$d_6$) using tetramethylsilane (TMS) as the internal standard. The value given is the chemical shift d in ppm.

Fluorinated 1,3-benzodioxoles of the formula

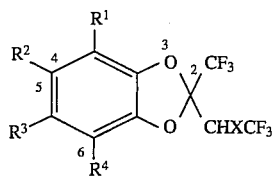

in which

X represents hydrogen, fluorine, chlorine or bromine, and $R^1$ and $R^4$ may be identical to or different from one another and in each case denote hydrogen, halogen, $C_1$–$C_6$-alkyl, $C_1$–$C_6$-alkoxy, halogeno-$C_1$–$C_6$-alkyl, $C_6$–$C_{10}$-aryl, COOH, CN, NCO, COO—$C_1$–$C_6$-alkyl, NH—$C_1$–$C_6$-alkyl, N($C_1$–$C_6$-alkyl)$_2$, and $R^2$ and $R^3$ represent $NO_2$ or $NH_2$, are obtainable by reacting 1,2-dihydroxybenzenes

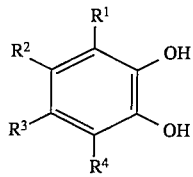

in which $R^1$ to $R^4$ have the meaning given above,
in the presence of a base and of a diluent at −20° to +200° C. with a hexfluorobutene of the formula

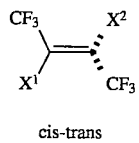

cis-trans in which $X^1$ represents hydrogen or halogen and $X^2$ represents halogen, or by reacting 1,2-dihydroxybenzenes which are provided with a protective group, of the formula

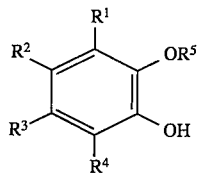

in which $R^1$ to $R^4$ have the meaning given above and $R^5$ represents a protective group or $R^5$ together with $R^1$ represents a —$C(CH_3)_2$—O— radical first with a hexafluorobutene of the formula

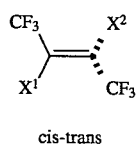

cis-trans in which $X^1$ represents hydrogen or halogen and $X^2$ represents halogen,
to obtain an intermediate of the formula

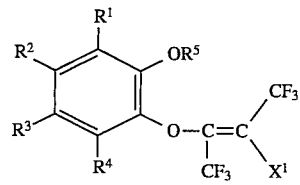

in which $R^1$ to $R^4$, $R^5$ and X have the meaning given above,
eliminating the protective group $R^5$ from the intermediate of the above formula,
and reacting the OH compound thus obtainable with a base, to obtain 1,3-benzodioxoles of the above formula.

1,3-Benzo-dioxoles which contain two adjacent amino groups can be converted with trifluoroacetic acid to the corresponding benzimidazole having, for example, the following formula

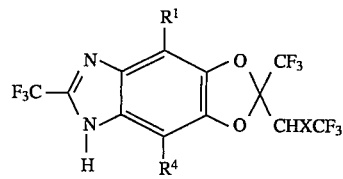

in which $R^1$, $R^4$ and X have the meaning given above.

From these compounds it is possible to obtain, by alkylation, benzimidazole derivatives which are substituted on the nitrogen atom with a

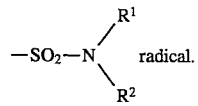

radical.

EXAMPLES

Example 1a 2-(2,2,2-Trifluoroethyl)-2-trifluoromethyl-1,3benzodioxole 11 g of pyrocatechol were dissolved in 200 ml of dimethylfomamide, and 18 g of 45% strength by weight aqueous sodium hydroxide solution were added. 20 g of 2-chloro-1, 1,1,4,4,4-hexafluoro-2-butene were added dropwise at 75° C. to the mixture. Stirring was continued for 30 minutes at 75° C. The mixture was then poured into 500 ml of ice-water and extracted with diethyl ether. The organic phase was washed with water, dried with magnesium sulphate and concentrated. Finally, the product was distilled under a high vacuum. The yield was 15 g (=56%) the boiling point was 60° C. at 10 mbar. The NMR spectra showed the following characteristic absorptions: $^{19}$F-NMR: −59.0 and −84.6 ppm; $^1$H-NMR: 3.02 ppm.

Example 2a 2-(1-Chloro-2,2,2-trifluoroethyl)-2-trifluoromethyl-1,3-benzodioxole 110 g of pyrocatechol were dissolved in 1,500 ml of acetonitrile, and 200 g of triethylamine were added. 235 g of 2,3-dichloro-1,1,1,4,4,4-hexafluoro-2-butene were added dropwise at 75° C. to the mixture. Stirring was continued for 2 hours at 75° C. 1,200 ml of the solvent were then distilled off in vacuo and the residue was taken up in 1,500 ml of water. The product was extracted with diethyl ether and the organic phase was washed 2 times with 10% strength by weight aqueous sodium hydroxide solution and 1 time with water. After drying with magnesium sulphate the product was concentrated and subjected to fractional distillation in vacuo. The yield was 258 g (=84% of theory). The boiling point was 63° C. at 12 mbar. The NMR spectra showed the following characteristic absorptions: $^{19}$F-NMR: −66.8 and −79.7 ppm; $^1$H-NMR: 4.71 ppm.

Examples 3a 2-(1,1,1,4,4,4-Hexafluoro-2-butenoxy)-methoxybenzene 260 g of 2-methoxyphenol were dissolved in 1 l of dimethylformamide (technical grade), and 220 g of 45% sodium hydroxide solution were added. Then 400 g of 2-chloro-1,1,1,4,4,4-hexafluoro-2-butene were added dropwise with stirring at 22° C. Stirring was continued for 2 hours at 22° C. Then 1.5 l of ice-water was added and the mixture was extracted with methylene chloride.

The combined organic phases were washed two times with 10% strength sodium hydroxide solution and once with saturated NaCl solution, dried with MgSO$_4$ and distilled. The yield was 329 g (58% of theory), the boiling point was 68°–70° C. at 12 mbar. The NMR spectra showed the following characteristic absorptions: $^{19}$F-NMR: −57.6 and −67.9 ppm; $^1$H-NMR: 5.92 ppm.

Example 4a 2-(1,1,1,4,4,4-hexafluoro-2-butenoxy)-phenol 286.1 g of 2-(1,1,1,4,4,4-hexafluoro-2-butenoxy)-methoxybenzene from Example 3a were dissolved in a mixture of 500 ml of glacial acetic acid and 500 ml of 48% strength hydrobromic acid, and 5 g of triethylbenzylammonium chloride were added. The mixture was stirred at a bath temperature of 150° C. until, according to gas-chromatographic monitoring, complete reaction had been achieved. The mixture was then allowed to cool, and 2 kg of ice-water were added. The aqueous phase was extracted thoroughly with CH$_2$Cl$_2$. After drying with MgSO$_4$ the solvent was stripped off and the residue was distilled in vacuo. The yield was 200 g (50% of theory), the boiling point was 80° C. at 16 mbar. The NMR spectra showed the following characteristic absorptions: $^{19}$F-NMR: −59.6 and −69.6 ppm; $^1$H-NMR: 6.1 ppm.

Example 5a 2-(2,2,2-Trifluoroethyl)-2-trifluoromethyl-1,3-benzodioxole 200 g of 2-(1,1,1,4,4,4-hexafluoro-2-butenoxy)-phenol from Example 4a were dissolved in 400 ml of acetonitrile, and 5 g of triethylamine were added. The mixture was stirred for 4 h at 70° C. Distillation was then carried out in vacuo. The yield was 162 g (81% of theory), the boiling point was 60° C. at 10 mbar. The NMR spectra showed the following characteristic absorptions: $^{19}$F-NMR: −59.0 and −84.6 ppm; $^1$H-NMR: 3.02 ppm.

Example, 6a 2-(2-Chloro-1,1,1,4,4,4-hexafluoro-2-butenoxy)-1-benzyloxybenzene 20 g of 2-benzyloxyphenol were dissolved in 100 ml of dimethylformamide, and 9 g of 45% strength sodium hydroxide solution were added. 23 g of 2,3-dichloro-1,1,1, 4,4,4-hexafluoro-2-butene were then added at room temperature. After the exothermic reaction had subsided the mixture was stirred for a further 1 hour at room temperature, placed in water and extracted with tert-butyl methyl ether. The mixture was dried with MgSO$_4$ and the solvent was then stripped off. The yield was 29 g (74% of theory). The NMR spectra showed the following characteristic absorptions: $^{19}$F-NMR: −59.5, −60.5, −61.7 and −62.8 ppm.

Example 7a 2-(2-Chloro-1,1,1,4,4,4-hexafluoro-2-butenoxy)-phenol 24.4 g of 2-(2-chloro-1,1,1,4,4,4-hexafluoro-2-butenoxy)-1-benzyloxybenzene from Example 6a were dissolved in 150 ml of tetrahydrofuran and treated at room temperature for 4 hours with 3 bar of hydrogen in the presence of 2 g of Pd/C (10%). The mixture was then filtered and the filtrate concentrated and distilled in vacuo. The yield was 13.2 g (69% of theory), the boiling point was 56° C. at 0.15 mbar.

Example 8a 2-(1-Chloro-2,2,2-trifluoroethyl)-2-trifluoromethyl-1,3-benzodioxole 11.7 g of 2-(2-chloro- 1,1,1,4,4,4-hexafluoro-2-butenoxy)-phenol from Example 7a were dissolved in 40 ml of tert-butyl methyl ether, and 40 ml of 1N sodium hydroxide solution were added. After stirring for 30 minutes at room temperature the organic phase was separated off, dried with MgSO$_4$ and distilled. The yield was 10 g (88% of theory), the boiling point was 63° C. at 12 mbar. The NMR spectra showed the following characteristic absorptions: $^{19}$F-NMR: −66.8 and −79.7 ppm; $^1$H-NMR: 4.71 ppm.

Example 9a 2,2-Dimethyl-4-(1,1,1,4,4,4-hexafluoro-2-butenoxy)-1,3-benzodioxole (formula V, R$^5$ together with R$^1$=—C(CH$_3$)$_2$—O— radical)

46 g of 2,2-dimethyl-4-hydroxy-1,3-benzodioxole (formula IV, R$^5$ together with R$^3$=—C(CH$_3$)$_2$—O— radical) were dissolved in 200 ml of N-methylpyrrolidone, and 31 g of 40% strength by weight aqueous sodium hydroxide solution were added. 54.8 g of 2-chloro-1,1,1,4,4,4-hexafluoro-2-butene were then added dropwise with stirring at room temperature. After further stirring for 1 hour the batch was poured into water and extracted with tert-butyl methyl ether. The organic phase was washed with 10% strength by weight aqueous sodium hydroxide solution and dried with magnesium sulphate, and the readily volatile fractions were removed on a rotary evaporator. There remained 73.8 g (=80% of theory) of a product which was 95% pure according to gas chromatography. The characteristic absorptions in the NMR spectra were: $^{19}$F-NMR: −58.1 and −68.5 ppm; $^1$H-NMR: 6.73, 6.55, 6.03 and 1.70 ppm.

Example 10a 1,2-Dihydroxy-3-(1,1,1,4,4,4-hexafluoro-2-butenoxy)-benzene 65 g of the product from Example 9a were heated to boiling, at reflux, with 200 ml of concentrated aqueous hydrochloric acid for 4 hours, while stirring. The mixture was then diluted with 300 ml of water and extracted with methylene chloride. After drying the extract with magnesium sulphate, the solvent was stripped off from the organic phase to give 54 g of a 90% pure product. Recrystallization from cyclohexane gave colourless crystals with a melting point of 105° C. The characteristic absorptions in the NMR spectra were as follows: $^{19}$F-NMR: −57.7 and −67.7 ppm; $^1$H-NMR: 6.77, 6.50, 6.21 and 5.42 ppm.

Example 11a 2-(2,2,2-Trifluoroethyl)-2-(trifluoromethyl)-4-hydroxy-1,3-benzodioxole (formula(I), $R^1$=OH, X=H, X=CH, $R^2$ and $R^3$=H).

43.5 g of the product from Example 10a were dissolved in 300 ml of acetonitrile, and 1.5 g of triethylamine was added at room temperature. After stirring for 2 hours at room temperature the solvent was stripped off and the residue distilled in vacuo. The yield was 17 g (=39% of theory), the boiling point was 85° C. at 0.15 mbar, and the melting point was 65° C. The characteristic absorptions in the NMR spectra were as follows: $^{19}$F-NMR: −59.0 and −84.5 ppm; $^1$H-NMR: 6.80, 6.55, 6.2 and 3.01 ppm.

Example 12a 2,2-Dimethyl-4-(3-chloro-1,1,1,4,4,4-hexafluoro-2-butenoxy)-1,3-benzodioxole (formula (V), $R^1$ and $R^5$ together are —C(CH$_3$)$_2$—O—, $X^1$=Cl, $R^2$+$R^3$=H, A=CH).

33.2 g of 2,2-dimethyl-4-hydroxy-1,3-benzodioxole were reacted in analogy to Example 9a with 47 g of 2,3-dichloro-1,1,1,4,4,4-hexafluoro-2-butene. The product obtained was distilled in vacuo, anda 1:1 molar mixture of cis/trans isomers was obtained. The yield was 51 g (=70% of theory), the boiling point was 70° C. at 0.15 mbar. The characteristic absorptions in the NMR spectra were as follows: $^{19}$F-NMR: −60.0, −61.6, −62.2 and 63.4 ppm; $^1$H-NMR: 6.79, 6.65 to 6.48 and 1.7 ppm.

Example 13a 1,2-Dihydroxy-3-(3-chloro-1,1,1,4,4,4-hexafluoro-2-butenoxy)-benzene(formula(V),$R^1$=OH, $R^2$+$R^3$=H, A=CH, $R^5$=H, $X^1$=Cl)

18 g of the product from Example 12a were reacted in analogy to Example 10a with 50 ml of concentrated hydrochloric acid. 15.7 g of a 97% pure product were obtained. The product was a 1:1 molar mixture of the cis/trans isomers. The characteristic absorptions in the NMR spectra were as follows: $^{19}$F-NMR: −60.2, −61.3, −62.2 and −63.3 ppm; $^1$H-NMR: 6.80, 6.45 and 6.25 ppm.

Example 14a 2-(1-Chloro-2,2,2-trifluoroethyl)-2-trifluoromethyl-4-hydroxy-1,3-benzodioxole 15 g of the product from Example 13a were dissolved in 50 ml of acetonitrile, and 1 ml of triethylamine was added. After stirring for 15 minutes, the solvent was stripped off and the residue was distilled in vacuo. For purification the product was taken up in diethyl ether and filtered over silica. After stripping off the diethyl ether there remained 10.5 g of the product (=70% of theory). The melting point was 139° to 141° C. The characteristic absorptions in the NMR spectra were as follows: $^{19}$F-NMR: −66.6 and −79.3 ppm; $^1$H-NMR: 8.4, 6.76, 6.60, 6.50 and 4.70 ppm.

Example 15a

5-Nitro-2-(2,2,2-trifluoroethyl)-2-trifluoromethyl-1,3-benzodioxole

A solution of 54.4 g of 2-(2,2,2-trifluoroethyl)-2-trifluoromethyl-1,3-benzodioxole in 75 ml of methylene chloride was added dropwise at 10° C. to a mixture of 40 ml of 65% strength by weight nitric acid and 40 ml of concentrated sulphuric acid. The mixture was stirred for a further 1 hour at room texture and then poured into ice-water, the organic phase was separated off and the aqueous phase was extracted with methylene chloride. The combined organic phases were washed with water, dried, and freed from readily volatile constituents. There remained 95 g of the product (=86% of theory) with a melting point of 87° to 88° C.

The NMR spectra showed the following characteristic absorptions: $^{19}$F-NMR: −59.0 and −69.4 ppm; $^1$H-NMR: 3.10 ppm.

Example 16a

5-Nitro-2-(1-chloro-2,2,2-trifluoroethyl)-2-trifluoromethyl-1,3-benzodioxole 613 g of 2-(1-chloro-2,2,2-trifluoroethyl)-2-trifluoromethyl-1,3-benzodioxole from Example 2a were dissolved in 1.2 l of methylene chloride, and the solution was added dropwise at 0° to 10° C. to a mixture of 400 ml of 65% strength nitric acid and 400 ml of concentrated sulphuric acid. The mixture was stirred for a further 2 hours at room temperature. It was then carefully placed in 2 l of ice-water and extracted with methylene chloride. The combined organic phases were washed 2 times with water, dried and concentrated. The yield was 652 g (93% of theory). The NMR spectra showed the following characteristic absorptions: $^{19}$F-NMR: −66.4 and −79.2 ppm; $^1$H-NMR: 4.81 ppm.

Example 17a 5,6-Dinitro-2-(2,2,2-trifluoroethyl)-2-trifluoromethyl-1,3-benzodioxole A mixture of 250 ml of 100% strength by weight nitric acid and 350 ml of concentrated sulphuric acid was added dropwise with stirring to an initial charge of 317 g of the product from Example 15a. The mixture was stirred for 2 hours at 55° C. The mixture was then cooled and poured into ice-water. The product was extracted with methylene chloride, washed until neutral with sodium hydrogen carbonate solution, dried, and freed on a rotary evaporator from readily volatile constituents. The yield was 339 g (=94% of theory), the melting point was 101° to 103° C.

The NMR spectra showed the following characteristic absorptions: $^{19}$F-NMR: −60.9 and −86.5 ppm; $^1$H-NMR: 3.18 ppm.

Example 18a 5,6-Dinitro-2-(1-chloro-2,2,2-trifluoroethyl)-2-trifluoromethyl-1,3-benzodioxole A mixture of 250 ml of 100% strength by weight nitric acid and 350 ml of concentrated sulphuric acid was added to an initial charge of 352 g of 5-nitro-2-(1-chloro-2,2,2-trifluoroethyl)-2-trifluoromethyl-1,3-benzodioxole from Example 16a. The mixture was stirred for 2 hours at 60° C. It was cooled, poured into ice-water and extracted with methylene chloride. After washing the mixture with sodium hydrogen carbonate solution and drying it was concentrated on a rotary evaporator. The yield was 392 g (91% of theory), the melting point was 125° C. The NMR spectra showed the following characteristic absorptions: $^{19}$F-NMR: −68.5 and −81.0 ppm; $^1$H-NMR: 4.86 ppm.

Example 19a

5-Amino-2-(2,2,2-trifluoroethyl)-2-trifluoromethyl-1,3-benzodioxole 57.4 g of the product from Example 15a were dissolved in 400 ml of tetrahydrofuran and hydrogenated in the presence of 4 g of catalyst (palladium on carbon, 10% by weight) for 5 hours at 30° C. at 50 bar with hydrogen. The mixture was then filtered, the solvent removed, and the remaining filtrate distilled under a high vacuum. 37 g of product (=63% of theory) were obtained with a boiling point of 83° C. at 0.07 mbar. $^{19}$F-NMR: −59.0 and −84.6 ppm; $^1$H-NMR: 2.98 ppm.

Example 20a

5-Amino-2-(1-chloro-2,2,2-trifluoroethyl)-2-trifluoromethyl-1,3-benzodioxole 72 g of 5-nitro-2-(1-chloro-2,2,2-trifluoroethyl)-2-trifluoromethyl-1,3-benzodioxole from Example 16a were dissolved in 500 ml of tetrahydrofuran, and hydrogenated using 5 g of palladium on carbon (5%) for 5 hours at room temperature with 15 to 20 bar of hydrogen. The mixture was then filtered and the solvent stripped off in vacuo. The yield was 60 g (93% of theory), the boiling point was 80° to 82° C. at 0.1 mbar. The NMR spectra showed the following characteristic absorptions: $^{19}$F-NMR: −66.5 and −79.4 ppm; $^1$H-NMR: 4.68 ppm.

Example 21a 5,6-Diamino-2-(2,2,2-trifluoroethyl)-2-trifluoromethyl-1,3-benzodioxole 339 g of the product from Example 17a were dissolved in 2,000 ml of tetrahydrofuran, and 20 g of catalyst (palladium on carbon, 5% by weight) were added. Hydrogenation was carried out with hydrogen at 25 to 30 bar for 13 hours at room temperature. The mixture was then filtered and the solvent stripped off in vacuo. A solid remained. The yield was 274 g (=96% of theory). $^{19}$F-NMR: −61.2 and −86.6 ppm; $^1$H-NMR: 3.02 ppm.

Example 22a 2-(2,2,2-Trifluoroethyl)-2-trifluoromethyl-1,3-benzodioxole 306.5 g of 2-(1-chloro-2,2,2-trifluoroethyl)-2-trifluoromethyl-1,3-benzodioxole from Example 2a were dissolved in 500 ml of THF, and 101 g of triethylamine and 30 g of palladium on carbon (5% by weight) were added. Hydrogenation was then carded out with 100 bar of hydrogen for 48 h at 110° C. The mixture was then filtered, the solvent stripped off and the residue subjected to fractional distillation in vacuo. The yield was 126 g (46% of theory), the boiling point was 60° C. at 10 mbar. The NMR spectra showed the following characteristic absorption: $^{19}$F-NMR: −59.0 and −84.6 ppm; $^1$H-NMR: 3.02 ppm.

o-Phenylenediamines containing fluoroalkyl(ene) groups, of the formula

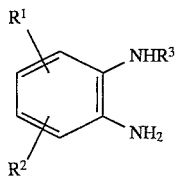

in which $R^1$ represents $CF_3$, $OCF_3$, $SCF_3$, $SO_2$-$C_1$-$C_6$-alkyl, which can be straight-chain or branched and may be substituted wholly or partially by fluorine, $N(CF_3)_2$, a phenyl or phenoxy radical with $CF_3$ or CN in the 4 position and optionally further substituents, 1,1,2,3,3,3-hexafluoropropoxy, 1,1,2-trifluoro-2-chloroethoxy, 1,1,2,2-tetrafluoroethoxy, 1,1,2-trifluoro-2-chloro-ethylthio or 1,1,2,3,3,3-hexafluoropropylthio, and independently thereof $R^2$ represents F, Cl, Br, CN, $CH_3$, $OCF_3$, $SO_2$-$C_1$-$C_6$-alkyl, which can be straight-chain or branched and may be substituted wholly or partially by fluorine, COO-$C_1$-$C_6$-alkyl, $COOC_6H_5$, 1,1,2,2-tetrafluoroethoxy, 1,1,2,3,3,3-hexafluoropropoxy or 1,1,2-trifluoro-2-chloroethoxy, and $R^3$ represents hydrogen, $COCH_3$ or $COCF_3$, where $R^1$ and $R^2$ can together represent a —O—CFCl—CFCl—O— radical, with the exception of the compounds described in EP-A 251 013 and EP-A 487 286, are obtainable by dinitrating a benzene derivative of the formula

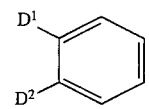

in which $D^1$ represents $CF_3O$, $CF_3S$, $CHF_2CF_2O$, $CHFCl$—$CF_2O$, $CF_3CHFCF_2O$, $CF_3CF_2O$, $CF_3CF_2CF_2O$, $CF_3CF_2S$ or $CF_3CHFCF_2O$, and $D^2$ represents $CF_3O$, $CF_3S$, $CHF_2CF_2O$, $CHFCl$—$CF_2O$, $CF_3CHF$—$CF_2O$, $CF_3CF_2O$, $CF_3CF_2CF_2O$, $CF_3CF_2S$ or $CF_3CHFCF_2O$, fluorine, chlorine, bromine, $C_1$-$C_6$-alkyl or $C_1$-$C_6$-alkoxy, and subsequently reducing the nitro groups to obtain compounds in which $R^1$ and $R^2$ are in the 4 and 5 positions with respect to the amino groups and have the meaning of $D^1$ and $D^2$.

If it is intended to prepare compounds in which $R^1$ has the meaning given above and is in the 4 position with respect to the amino groups, and $R^2$ represents Cl or Br and is in the 5 position with respect to the amino groups, then, for example, a nitrobenzene derivative of the formula

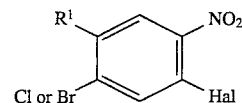

in which $R^1$ has the meaning given and

Hal represents fluorine, chlorine or bromine, can be reacted with ammonia, the Hal group thus exchanged for an amino group, and the resulting nitroaniline can be reduced.

If it is intended to prepare compounds in which $R^1$ has the meaning given above and is in the 4 position with respect to the amino groups, $R^2$ represents chlorine or bromine and is in the 6 position with respect to the amino groups and $R^3$ denotes hydrogen, then, for example, a nitroaniline of the formula

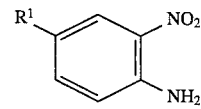

in which $R^1$ has the meaning given above can be reacted with a chlorinating or brominating agent, a chlorine or bromine atom thus introduced into the position meta to the nitro group, and subsequently the nitro group can be reduced.

If it is intended to prepare compounds in which $R^1$ represents a donor group in the 4 position with respect to the two amino groups, $R^2$ represents an acceptor group, e.g. COO-$C_1$–$C_6$-alkyl, CN, $CF_3$ or $SO_2$-$C_1$–$C_6$-alkyl, and $R_3$ is not hydrogen then, for example, a benzene derivative of the formula

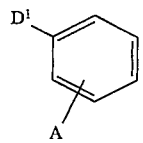

in which $D^1$ has the meaning given above and

A represents $CF_3$, $SO_2C_1$–$C_6$-alkyl which is straight-chain or branched and may be substituted wholly or partially by fluorine, COO-$C_1$–$C_6$-alkyl or CN, can be mononitrated (introduction of the $NO_2$ group into the position para to $D^1$), the $NO_2$ group can be reduced to the $NH_2$ group, the $NH_2$ group can be acylated with, for example, acetic acid or trifluoroacetic acid, the product can again be mononitrated (introduction of this $NO_2$ group into the position ortho to the NHCOR groups where R=e.g. $CH_3$ or $CF_3$), this $NO_2$ group can be reduced to the $NH_2$ group and optionally, if it is desired to prepare a compound of the above formula where $R^3$=hydrogen, the acyl group can be eliminated by hydrolysis.

The o-phenylenediamines containing fluoroalkyl(ene) groups, in which $R^3$ denotes hydrogen, can initially be reacted with trifluoroacetic acid to give 2-trifluoromethyl-benzimidazoles of the formula

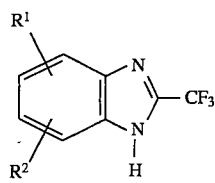

and then further reacted with compounds of the formula

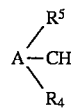

where $R^1$ and $R^2$ adopt the above scope of meaning, $R^4$ represents hydrogen, alkyl, alkoxy or optionally substituted aryl, $R^5$ represents hydroxyl, cyano or in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy, and A denotes a suitable leaving group.

Leaving groups are known to those skilled in the art and are, for example, halogen, alkyl(alkoxy, aryl)sulphonyloxy, hydroxyl or alkoxy.

EXAMPLES

Examples 1b to 6b (Dinitration and reduction)

Example 1b 320 g of 1,2-bis-(2-chloro-1,1,2-trifluoroethoxy)-benzene were added dropwise to 500 g of a mixed acid containing 33% by weight of $HNO_3$ and 67% by weight of $H_2SO_4$. After one hour at 40° C. 250 ml of 20% strength by weight oleum were added dropwise. The mixture was then heated to 80° C. and stirred for 15 hours. Subsequently a further 120 ml of 20% strength by weight oleum and. 250 g of the abovementioned mixed acid were added dropwise. After 6 hours at 80° to 82° C. the mixture was cooled and poured onto ice. The organic phase was separated off and washed with water. After azeotropic drying with 1,2-dichloroethane, 350 g of 96% by weight pure 1,2-dinitro-4,5-bis-(2-chloro-1,1,2-trifluoroethoxy)-benzene were obtained (oil, $n_D^{20}$: 1.4832, GC 99.1%).

350 g of this dinitro compound were added dropwise to a mixture of 1.5 l of ethanol, 50 ml of water, 30 ml of concentrated aqueous hydrochloric acid and 470 g of iron filings, and heated to boiling at reflux for a total of 15 hours. The solution was subsequently cooled and filtered, the filtrate concentrated, and the residue recrystallized from cyclohexane. 216 g of 1,2-diamino-4,5-bis-(2-chloro-1,1,2-trifluoroethoxy)-benzene having a melting point of 58 to 60° C. were obtained.

Example 2b

In analogy to Example 1, from 1,2-bis-(1,1,2,3,3,3-hexafluoropropoxy)-benzene, the corresponding 4,5-dinitro compound (oil, $n_D^{20}$: 1.4852) and the corresponding 4,5-diamino compound (oil, 87% by weight pure) were prepared.

Example 3b

In analogy to Example 1, from 1-(1,1,2-1trifluoro-2-chloroethoxy)-2-chlorobenzene, the corresponding 4,5-dinitro compound (melting point 56 to 57° C.) and the corresponding 4,5-diamino compound (melting point 67° to 68° C.) were prepared.

Example 4b

In analogy to Example 1, from 1-trifluoromethoxy-2-bromobenzene, the corresponding 4,5-dinitro compound (melting point 73° to 75° C.) and the corresponding 4,5-diamino compound (oil, 98% by weight pure, $n_D^{20}$: 1.5485) were prepared.

Example 5b

In analogy to Example 1, from 1-trifluoromethoxy-2-chlorobenzene, the corresponding 4,5-dinitro compound (melting point 55° to 56° C.) and the corresponding 4,5-diamino compound (melting point 56°–57° C.) were prepared.

Example 6b

From 1-(1,1,2,3,3,3-hexafluoropropoxy)-2-chloro-benzene, the corresponding 4,5-dinitro compound (oil) and the corresponding 4,5-diamino compound (oil) were prepared.

Examples 7b to 12b

Pressurization with ammonia and reduction

Example 7b 260 g of 3-nitro-2,5-dichlorobenzotrifluoride, 130 ml of water and 10 g of tetraethylammonium chloride were placed in an autoclave, and 120 ml of liquid ammonia were injected. The mixture was then heated to 130° C. and stirred for 10 hours at this temperature. The mixture was cooled and then filtered, and the precipitate separated off was washed with water and dried. 194 g of 2-amino-3-nitro-5-chlorobenzotrifluoride with a melting point of 67° C. were obtained. 134 g of the nitroaniline obtained as described above were dissolved in 800 ml of ethanol, and then 20 ml of water, 10 ml of concentrated aqueous hydrochloric acid and 160 g of iron filings were added. The mixture was heated for 15 hours to boiling at reflux, then cooled and filtered off with suction, the filter residue was washed with dichloromethane, and subsequently the organic phases were freed under reduced pressure from the solvent. 171 g of 5-chloro-3-trifluoromethyl-1,2-diaminobenzene with a melting point of 53° C. were obtained.

Example 8b

In analogy to Example 7, from 3-nitro4,6-dichloro-difluorochloromethoxybenzene, initially 3-nitro-4-amino-6-chloro-difluorochloromethoxybenzene (melting point 73° C.) were obtained, from which 3,4-diamino-6-chloro-difluorochloromethoxybenzene (oil) was obtained.

Example 9b

In analogy to Example 7, from 3-bromo-5-nitro-6-chlorobenzotrifluoride, initially 3bromo-5-nitro-6-amino-benzotrifluoride (melting point 80° to 82° C.) was prepared, from which 3-bromo-5,6-diamino-benzotrifluoride (melting point 52° to 54° C.) was prepared

Example 10b

In analogy to Example 7, from 3-cyano4-chloro-5-nitrobenzotrifluoride, initially 3-cyano-4-amino-5-nitro-benzotrifluoride (melting point 99° to 100° C.) was prepared, from which 3-cyano-4,5-diamino-benzotrifluoride was prepared.

Example 11b

In analogy to Example 7, from 3,6-dichloro-5-nitro-benzotrifluoride, initially 3-chloro-5-nitro-6-amino-benzotrifluoride (melting point 53° to 54° C.) was prepared, from which 3-chloro-5,6-diamino-benzotrifluoride was prepared.

Example 12b

From 2-bromo4-fluoro-5-nitro-(1,1,2-trifluoro-2-chloro)-ethoxybenzene, initially 2-bromo-4-amino-5-nitro-(1,1,2-trifluoro-2-chloro-ethoxy)-benzene (melting point 90° C.) was prepared, from which 2-bromo-4,5-diamino-(1,1,2-trifluoro-2-chloro)-ethoxybenzene was prepared.

Example 13b (Halogenation of a nitroaniline and reduction)

24 g of freely powdered 2-nitro4-trifluoromethylmercaptoaniline were dissolved in 50 ml of trifluoroacetic acid, and 18 g of bromine were metered in at 20° C. The mixture was then stirred for 3 hours at 20° C. and for a further 30 minutes at 40° C. The mixture was placed in water and the product was taken up in dichloromethane. After removal of the solvent, 31 g of 6-bromo-2-nitro-4-trifluoromethyl-mercapto-aniline were obtained.

155 g of the nitroaniline thus prepared were heated in 700 ml of ethanol to boiling at reflux for 15 hours with 15 ml of water, 10 ml of concentrated aqueous hydrochloric acid and 70 g of iron filings; the mixture was then filtered, the filtrate freed from solvent under reduced pressure, and the crude solid product recrystallized from cyclohexane. 112 g of 6-bromo-4-trifluoromethyl-mercapto-1,2-diaminobenzene with a melting point of 60° to 61° C. were obtained. cl Example 14b In analogy to Example 13, 27 g of 2-nitro-4-trifluoromethyl-sulphonylaniline in 100 ml of acetic acid were brominated with 18 g of bromine.

After work-up, 32 g of 2-nitro-6-bromo-4-trifluoro-methylsulphonyl-anialine were obtained: melting point 147° C.

32 g of the nitroamine thus prepared was reduced with iron filings in alcohol and aqueous hydrochloric acid. 24 g of 3-bromo-5-trifluoromethylsulphonyl-phenylene-1,2-diaminine were obtained; melting point 155°–157° C.

Example 15b

In analogy to Example 14, 27 g of 2-nitro-4-trifluoromethylsulphonyl-aniline in 100 ml of acetic acid were chlorinated with 10 g of chlorine. 29 g of 2-nitro4-trifluoromethylsulphonyl-6-chloro-aniline were obtained; melting point 138°–139° C.

By reduction, 13 g of 3-chloro-5-trifluoromethylsulphonyl-1,2-phenylenediamine (melting point: 143°–145° C.) were obtained.

Example 16 to 20

(Nitration and reduction in 2 stages)

Example 16b 263 g of 4-(2,6-dichloro-4-trifluoromethyl)-phenoxy-acetanilide were dissolved in 1,100 ml of dichloromethane, and taken as initial charge at 10° C. 88 g of 98% strength by weight nitric acid were then added dropwise at this temperature. The mixture was stirred for 1 hour at 10° C. and 2 further hours at 30° C. After the addition of 300 ml of water, the phases were separated and the organic phase was freed from dichloromethane under reduced pressure. There remained 253 g of 2-nitro-4-(2,6 dichloro-4-trifluoromethyl)phenoxy)-acetanilide with a melting point of 138°–140° C.

91 g of the acetanilide thus prepared were dissolved in 800 ml of dioxane, 10 g of Raney nickel were added, and hydrogenation was carried out at 25 to 45° C. in a hydrogenation apparatus with a maximum of 50 bar hydrogen pressure. The apparatus was let down, the mixture was filtered, and the dioxane was distilled off under a slight vacuum. There remained 65 g of 2-amino-4-(2,6-dichloro-4-trifluoromethyl-phenoxy)-acetanilide with a melting point of 222°–223° C.

Example 17b

In analogy to Example 16, from 3-trifluoromethyl-4-methoxy-acetanilide, initially 3-trifluoromethyl-4-methoxy-6-nitro-acetanilide (melting point 143°–144° C.) was prepared, from which 3-trifluoromethyl-4-methoxy-6-amino-acetanilide (melting point 164–°165° C.) was prepared.

Example 18b

In analogy to Example 16, from 3-trifluoromethyl-4-fluoro-trifluoromethylacetanilide, initially 3-trifluoromethyl-4-fluoro-6-nitro-trifluoromethylacetanilide (melting point 78° C.) was prepared, from which 3-trifluoromethyl-4-fluoro-6-aminotrifluoromethylacetanilide (melting point 92°–93° C.) was prepared.

Example 19b

In analogy to Example 16, from 3-trifluoromethyl-4-bromo-trifluoromethylacetanilide, initially 3-trifluoromethyl-4-bromo-6-nitro-trifluoromethylacetanilide (melting point 110°–112° C.) was prepared, from which 3-trifluoromethyl-4-bromo-6-aminotrifluoromethylacetanilide (melting point 63°–65° C.) was prepared.

Example 20b

In analogy to Example 16, from 3-trifluoromethylthio-4-chloro-trifluoromethylacetanilide, initially 3-trifluoromethylthio-4-chloro-6-nitrotrifluoromethylacetanilide (melting point 99°–100° C.) was prepared, from which 3-trifluoromethylthio-4-chloro-6-amino-trifluoromethylacetanilide (melting point 88°–90° C.) was prepared.

Example 21 b 0.2 mol of 3-bromo-5-trifluoromethyl-phenylene-diamine were heated with 150 ml of trifluoroacetic acid for 3 hours at reflux temperature. For working up, excess trifluoroacetic acid was distilled off and the residue was partitioned between 100 ml of water and 300 ml of ethyl acetate. The organic phase was separated off, washed successively with in each case 100 ml of aqueous sodium hydrogen carbonate solution and water, dried over sodium sulphate, and concentrated in vacuo. The residue was purified by chromatography on silica gel (eluent: cyclohexane/ethyl acetate 1:1).

4-Bromo-6-trifluoromethyl-2-trifluoromethyl-1H-benzimidazole with a melting point of 149°–151° C. was obtained.

Example 22b 0.03 mol of 4-bromo-6-trifluoromethyl-2-trifluoromethyl-1H-benzimidazole and 0.06 mol of powdered potassium carbonate were heated in 70 ml of ethyl acetate for 15 minutes at reflux temperature; 3.9 g (0.04 tool) of chloromethyl methyl thioether in 20 ml of ethyl acetate were then added, and the mixture was heated with stirring for a further 4 hours at reflux temperature. For working up, the reaction mixture was cooled and washed twice with in each case 40 ml of water, dried over sodium sulphate and concentrated in vacuo, and the residue was purified by chromatography on silica gel (eluent: dichloromethane).

1-Methylthiomethyl-4-bromo-6-trifluoromethyl-2-trifluoromethyl-benzimidazole with a melting point of 56°–60° C. was obtained.

APPLICATION EXAMPLES

In the following Application Examples, the compounds listed below were employed as comparison substances:

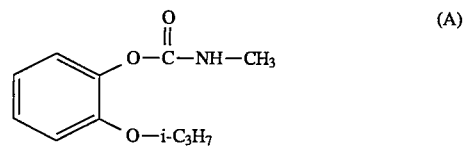

N-Methyl-O-(2-isopropoxyphenyl)-carbamate (cf. e.g. DE 11 08 202)

O,S-Dimethyl-thiolo-phosphoramide (cf. e.g. DE 12 10 835)

Example A

Plutella Test:

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired time, the destruction in per cent is determined. 100% means that all the caterpillars have been killed; 0% means that none of the caterpillars have been killed.

In this test, for example the following compound from the Preparation Examples exhibits superior activity over the prior art: 12, 15, 16 and 19.

TABLE A

Plutella test

| Active substances | | Concentration of active substance in % | Degree of destruction in % after 3 days |
|---|---|---|---|
| 2-isopropoxyphenyl N-methylcarbamate (known) | (A) | 0.1<br>0.01<br>0.001 | 100<br>100<br>10 |
| 5-Br-6-CF₃ and 5-CF₃-6-Br benzimidazole N-sulfonyl dimethylamide mixture with 2-CF₃ | (12) | 0.1<br>0.01<br>0.001 | 100<br>100<br>100 |
| 5,6-(OCF₂CF₂O)-2-CF₃-benzimidazole-1-sulfonyl dimethylamide | (15) | 0.1<br>0.01<br>0.001 | 100<br>100<br>100 |
| 5,6-(OCF₂CFHO)-2-CF₃-benzimidazole-1-sulfonyl dimethylamide | (16) | 0.1<br>0.01<br>0.001 | 100<br>100<br>100 |
| 5,6-(OCFHCF₂O)-2-CF₃-benzimidazole-1-sulfonyl dimethylamide | | | |
| 5,6-bis(OCF₃)-2-CF₃-benzimidazole-1-sulfonyl dimethylamide | (19) | 0.1<br>0.01<br>0.001 | 100<br>100<br>100 |

Example B

Heliothis virescens test

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya shoots (*Glycine max*) are treated by being dipped into the preparation of active compound of the desired concentration and are infested with tobacco budworms (*Heliothis virescens*) while the leaves are still moist.

After the desired time, the destruction in per cent is determined. 100% means that all the worms have been killed; 0% means that none of the worms have been killed.

In this test, for example the following compound from the Preparation Examples exhibits superior activity over the prior art: 1, 7, 10, 11, 12, 13, 15, 17, 18 and 26.

TABLE B

Heliothis virescens test

| Active substances | | Concentration of active substance in % | Degree of destruction in % after 3 days |
|---|---|---|---|
| [structure: phenyl with O-C(=O)-NH-CH₃ and O-i-C₃H₇] (known) | (A) | 0.1 | 10 |
| [structure: benzimidazole with Br, CF, 2-CF₃, N-SO₂-N(CH₃)₂] | (1) | 0.1 | 100 |
| [structure: benzimidazole with F₃C, 2-CF₃, N-SO₂-N(CH₃)₂] | (10) | 0.1 | 100 |
| [structure: benzimidazole with F₃C, 2-CF₃, N-SO₂-N(CH₃)₂] | | | |
| [structure: benzimidazole with F₃C, 2-CF₃, N-SO₂-NH-CH(CH₃)₂] | (11) | 0.1 | 100 |

TABLE B-continued

Heliothis virescens test

| Active substances | | Concentration of active substance in % | Degree of destruction in % after 3 days |
|---|---|---|---|
| [Structure: 5-CF₃ benzimidazole, 2-CF₃, 1-SO₂—NH—CH(CH₃)(CF₃)] | | | |
| [Structure: 5-Br, 6-F₃C benzimidazole, 2-CF₃, 1-SO₂—N(CH₃)₂] + [Structure: 5-F₃C, 6-Br benzimidazole, 2-CF₃, 1-SO₂—N(CH₃)₂] | (12) | 0.1 | 100 |
| [Structure: 5-Cl, 6-F₃C benzimidazole, 2-CF₃, 1-SO₂—NH—CH(CH₃)(CF₃)] + [Structure: 5-F₃C, 6-Cl benzimidazole, 2-CF₃, 1-SO₂—NH—CH(CH₃)(CF₃)] | (13) | | |
| [Structure: methylenedioxy-difluoro benzimidazole, 2-CF₃, 1-SO₂—N(CH₃)₂] | (15) | 0.1 | 100 |
| [Structure: F₃CO-benzimidazole, 2-CF₃, 1-SO₂—N(CH₃)₂] + [Structure: F₃CO-benzimidazole isomer, 2-CF₃, 1-SO₂—N(CH₃)₂] | (18) | 0.1 | 100 |

TABLE B-continued

Heliothis virescens test

| Active substances | | Concentration of active substance in % | Degree of destruction in % after 3 days |
|---|---|---|---|
| [Structure: benzimidazole with $F_3CS$ substituent, $CF_3$ at 2-position, and $SO_2-N(CH_3)_2$ on N1] | (26) | 0.1 | 100 |
| + | | | |
| [Structure: benzimidazole with $F_3C$ substituent, $CF_3$ at 2-position, and $SO_2-N(CH_3)_2$ on N1] | | | |

Example C

| Tetranychus test (OP-resistant) | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily Nested with all developmental stages of the red spider mite (*Tetranychus urticae*) are dipped in a preparation of the active compound of the desired concentration.

After the desired time, the destruction in per cent is determined. 100% means that all the spider mites have been killed; 0% means that none of the spider mites have been killed.

In this test, for example the following compounds from the Preparation Examples exhibit superior activity over the prior art: 12 and 14.

TABLE C

Tetranychus test (OP-resistant)

| Active substances | | Concentration of active substance in % | Degree of destruction in % after 7 days |
|---|---|---|---|
| $CH_3O-\underset{\underset{SCH_3}{\mid}}{\overset{\overset{O}{\|}}{P}}-NH_2$ (known) | (B) | 0.01 | 60 |
| [Structure: benzimidazole with Br and $F_3C$ substituents, $CF_3$ at 2-position, and $SO_2-N(CH_3)_2$ on N1] | (12) | 0.01 | 100 |
| + | | | |

TABLE C-continued

Tetranychus test (OP-resistant)

| Active substances | | Concentration of active substance in % | Degree of destruction in % after 7 days |
|---|---|---|---|
| 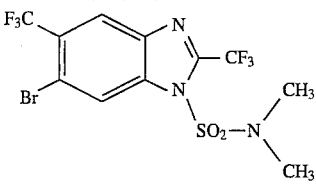 | | | |
| 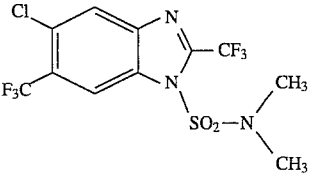 | (14) | 0.01 | 100 |
| 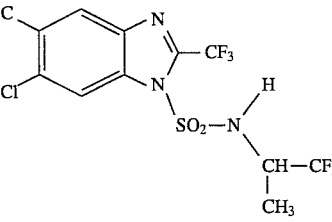 | | | |

Example D

Psoroptes ovis test:

| | |
|---|---|
| Solvent: | 35 parts by weight of ethylene glycol monomethyl ether |
| Emulsifier: | 35 parts by weight of nonylphenol polyglycol ether |

To produce a suitable preparation of active compound, 3 parts by weight of active compound are mixed with 7 parts of the solvent/emulsifier mixture indicated above, and the emulsion concentrate thus obtained is diluted with water to the desired concentration.

1 ml of this active compound preparation is pipetted into suitably sized PP blister packs. About 25 mites are then transferred to the active compound preparation.

After 24 hours the effectiveness of the active compound preparation is determined in %. 100% means that all the mites have been killed; 0% means that none of the mites have been killed.

In this test, for example the following compounds from the Preparation Examples exhibit superior activity over the prior art: 12, 15 and 26.

TABLE D

Psoroptes ovis test

| Active substances | | Concentration of active substance in ppm a.i. | Degree of destruction in % |
|---|---|---|---|
| 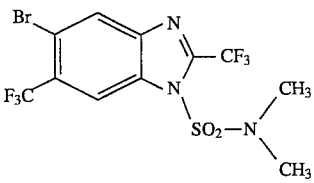 | (12) | 10 | 100 |
| | | 1 | 100 |

+

TABLE D-continued

Psoroptes ovis test

| Active substances | Concentration of active substance in ppm a.i. | Degree of destruction in % |
|---|---|---|
| [structure: 5-CF$_3$, 6-Br benzimidazole with 2-CF$_3$ and N-SO$_2$-N(CH$_3$)$_2$] (15) | 10 | 100 |
| [structure: 5,6-(OCF$_2$CF$_2$O) benzimidazole with 2-CF$_3$ and N-SO$_2$-N(CH$_3$)$_2$] (26) | 10 | 100 |
| [structure: 6-CF$_3$ benzimidazole with 2-CF$_3$ and N-SO$_2$-N(CH$_3$)$_2$] + [structure: 6-SCF$_3$ benzimidazole with 2-CF$_3$ and N-SO$_2$-N(CH$_3$)$_2$] | | |

Example E

| Periplaneta americana test: | |
|---|---|
| Solvent: | 35 parts by weight of ethylene glycol monomethyl ether |
| Emulsifier: | 35 parts by weight of nonylphenol polyglycol ether |

To produce a suitable preparation of active compound, 3 parts by weight of active compound are mixed with 7 parts of the solvent/emulsifier mixture indicated above, and the resulting emulsion concentrate is diluted with water to the desired concentration.

2 ml of this active compound preparation are pipetted onto filter paper discs (diameter: 9.5 cm) in suitably sized Petri dishes. After drying the filter discs, five cockroaches (*Periplaneta americana*) are transferred to the Petri dishes and covered.

After 3 days the effectiveness of the active compound preparation is determined in %. 100% means that all the cockroaches have been killed; 0% means that none of the cockroaches have been killed.

In this test, for example the following compounds from the Preparation Examples exhibit superior activity over the prior art: 6, 10, 14, 15 and 26.

TABLE E

Periplaneta americana test

| Active substances | | Concentration of active substance in ppm a.i. | Degree of destruction in % |
|---|---|---|---|
| [Structure: 6-nitro-2-(trifluoromethyl)-1-(N,N-dimethylsulfamoyl)benzimidazole] + [Structure: 5-nitro isomer] | (6) | 1000 | 100 |
| [Structure: 6-CF$_3$-2-CF$_3$-1-(N,N-dimethylsulfamoyl)benzimidazole] + [Structure: 5-CF$_3$ isomer] | (10) | 1000<br>100 | 100<br>>50 |
| [Structure: 5-Cl-6-CF$_3$-2-CF$_3$-1-(N,N-dimethylsulfamoyl)benzimidazole] + [Structure: 5-CF$_3$-6-Cl isomer] | (14) | | |
| [Structure: 5,6-(OCF$_2$CF$_2$O)-2-CF$_3$-1-(N,N-dimethylsulfamoyl)benzimidazole] | (15) | | |

5,585,395

TABLE E-continued

Periplaneta americana test

| Active substances | | Concentration of active substance in ppm a.i. | Degree of destruction in % |
|---|---|---|---|
| 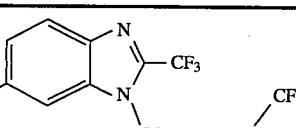 | (26) | | |

Example F

Musca domestica test:

| Solvent: | 35 parts by weight of ethylene glycol monomethyl ether |
|---|---|
| Emulsifier: | 35 parts by weight of nonylphenol polyglycol ether |

To produce a suitable preparation of active compound, 3 parts by weight of active compound are mixed with 7 parts of the solvent/emulsifier mixture indicated above, and the resulting emulsion concentrate is diluted with water to the desired concentration.

2 ml of this active compound preparation are pipetted onto filter paper discs (diameter: 9.5 cm) in suitably sized Petri dishes. After drying the filter discs, 25 test organisms (*Musca domestica*, strain WHO [N]) are transferred to the Petri dishes and covered.

After 3 days the effectiveness of the active compound preparation is determined in %. 100% means that all the flies have been killed; 0% means that none of the flies have been killed.

In this test, for example the following compounds from the Preparation Examples exhibit superior activity over the prior art: 5.

TABLE F

Musca domestica test

| Active substances | | Concentration of active substance in ppm a.i. | Degree of destruction in % |
|---|---|---|---|
| 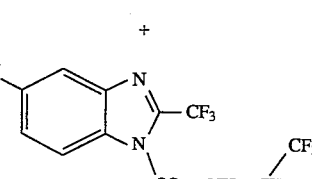 | (5) | 1000<br>100 | 100<br>>50 |

We claim:

1. A method for combating plant damaging insects and mites comprising applying to a host plant infested with said insects or mites an amount effective therefor of a substituted benzimidazole of the general formula (I)

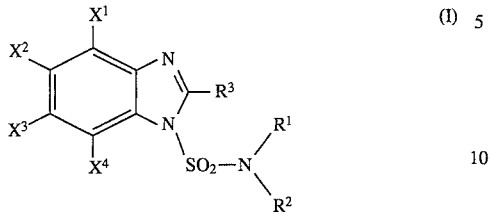

in which

R¹ represents hydrogen, alkyl, halogenoalkyl, cycloalkyl or optionally substituted aryl, R² represents hydrogen, alkyl, halogenoalkyl, cycloalkyl or optionally substituted aryl, R³ represents fluoroalkyl and X¹, X², X³ and X⁴ independently of one another in each case represent hydrogen, halogen, cyano, in each case optionally substituted alkyl, alkoxy, alkylthio, alkylsulphinyl, alkylsulphonyl or cycloalkyl, dioxyalkylene which is optionally substituted and may be fused on, hydroxycarbonyl, alkylcarbonyl, alkoxycarbonyl, cycloalkyloxycarbonyl, in each case optionally substituted amino or aminocarbonyl or in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but with at least one of the substituents X¹, X², X³ and X⁴ being different from hydrogen.

2. The method of claim 1, wherein said substituted benzimidazole is applied as a solution containing from 0.1 to 95% by weight of said benzimidazole in a solvent.

3. The method of claim 1, wherein said benzimidazole is applied in the form of a composition comprising an effective amount of said benzimidazole an extender, a surface active agent or both an extender and a surface active agent.

* * * * *